(12) United States Patent
Syroid et al.

(10) Patent No.: US 8,744,779 B2
(45) Date of Patent: Jun. 3, 2014

(54) METHODS AND APPARATUS FOR DRUG MODELING AND DISPLAYING DRUG MODELS

(75) Inventors: Noah Syroid, Salt Lake City, UT (US); Dwayne R. Westenskow, Salt Lake City, UT (US); James Agutter, Salt Lake City, UT (US); Talmage D. Egan, Salt Lake City, UT (US); Kenward B. Johnson, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/360,642

(22) Filed: Jan. 27, 2012

(65) Prior Publication Data

US 2012/0197188 A1 Aug. 2, 2012

Related U.S. Application Data

(62) Division of application No. 11/725,864, filed on Mar. 20, 2007, now abandoned.

(51) Int. Cl.
*G01N 33/50* (2006.01)
*G06F 19/00* (2011.01)

(52) U.S. Cl.
CPC ........ *G06F 19/3437* (2013.01); *G06F 19/3456* (2013.01)
USPC .......................................... 702/19

(58) Field of Classification Search
None
See application file for complete search history.

(56) References Cited

U.S. PATENT DOCUMENTS

2003/0156143 A1* 8/2003 Westenskow et al. ........ 345/848

* cited by examiner

*Primary Examiner* — Jason Sims
(74) *Attorney, Agent, or Firm* — Thorpe North & Western LLP

(57) ABSTRACT

Drug delivery models, displays, and systems may be configured to provide a clinician with readily intuitive information about the effects of one or more drugs on a subject. Interactive features may be included to provide a subject-specific model of the expected or predicted effects of one or more drugs on the subject. Additionally, interactive features that effect drug delivery to the subject may also be included. Drug delivery models, displays, and systems may be used in teaching, in advance of treatment, during treatment, or following treatment.

20 Claims, 10 Drawing Sheets

METHODS AND APPARATUS FOR DRUG MODELING AND DISPLAYING DRUG MODELS

FEDERAL RESEARCH STATEMENT

Some of the technology described in this patent application was funded in part by National Institute of Health grant number 1R24 HL 64590.

FIELD OF THE INVENTION

The present invention relates generally to methods and apparatus for evaluating the combined effects of two or more drugs on a subject and, more specifically, to methods and apparatus for graphically evaluating and displaying the combined effects of two or more anesthetic agents on a subject.

BACKGROUND OF THE INVENTION

Clinical pharmacology is the science of predicting the magnitude and time course (e.g., pharmacokinetics, or $P_k$) of drug effect. Given that anesthetists spend their day administering low therapeutic index agents, clinical pharmacology is perhaps more important to anesthesiology than any other specialty. Anesthesia and reanimation necessitate a standard of precision and accuracy in drug administration not required in most areas of clinical medicine. Anesthetists depress the central nervous system to maintain the anesthetized state but then rapidly reanimate patients after an operation is complete. Although over-dosing every patient within the constraints of acceptable hemodynamic variables is one approach to assuring the patient is adequately anesthetized, it comes at the cost of slow emergence from anesthesia. The anesthetist must rely on drugs with rapid onset and predictable offset of effect to ensure maintenance of an anesthetic state with return of responsiveness and other vital function until the appropriate time. Anesthetists must therefore target drug levels that are within a relatively narrow therapeutic window to achieve the competing clinical imperatives of adequate anesthesia (without toxicity) and rapid emergence. Thus, from a practical aspect, the ultimate goal of clinical pharmacology is to provide anesthetists with the information they need to make rational and rapid decisions about the selection and administration of anesthetics.

Apparatus for modeling and displaying the modeled effects of a single drug on a subject are known in the art. These apparatus are useful in assisting those administering drugs, including health care professionals and other individuals, as well as automated systems that deliver drugs, with information that is useful in determining if, when, and how much of an additional dosage of the drug should be administered to the subject. Conventionally, such apparatus were configured to model the concentration of the drug in a subject's body, or "pharmacokinetics" ($P_k$) of the drug. More recently, modeling techniques and apparatus have been used to model the effect site concentration of the drug, or "pharmacodynamic effect" or "pharmacodynamics" ($P_d$) of the drug, which is a measure of the effectiveness of the drug on the body of a subject, may be modeled over time. Unfortunately, the often puzzling mathematical manipulations involved in estimating pharmacokinetic and pharmacodynamic parameters and the complex math required to build models that predict drug behavior have made use of these models in a clinical setting impractical.

As multiple drugs may be administered to a subject, more than one drug may have an effect on a patient or other subject during a particular point in time. Further, when multiple drugs are present in the body of a subject, they may have an effect on one another, or affect the subject in a different manner than any of the drugs alone would affect the subject. Nonetheless, modeling apparatus and techniques that are known in the art do not account for drug-drug interactions, or the combined effects of two or more drugs on the body of a subject.

Modeling techniques and apparatus that are known to the named inventors of the claimed subject matter do not consider the individual characteristics of a subject to which drugs are administered, the effects of multiple drugs on one another, or the effects of multiple drugs on a subject to which they are administered.

Without multiple sources of pharmacodynamic knowledge and monitoring, excessive dosages may waste drugs and, thus, money; prolong withdrawal of the subject from anesthesia, which may consume the availability of valuable operating room time; and even cause death of the subject. When anesthesia dosages are too small, the subject may become conscious or semi-conscious during an operation or other invasive procedure or the subject may be required to endure an excessive amount of pain, both of which may have a number of other negative consequential effects on the subject.

Moreover, anesthetists have been unable to effectively integrate the intricacies of kinetics and dynamics into their clinical practice, and instead, rely on training and experience to determine dosing.

Accordingly, there is a need in the art for techniques and apparatus that provide those who administer drugs or monitor the administration of drugs, in an intuitive manner, with additional information that would be beneficial in determining the proper amounts of one or more drugs that should be administered to a subject.

SUMMARY OF THE INVENTION

The present invention includes methods that relate to the simultaneous administration of two or more drugs to a subject, including evaluation of the synergism or antagonism of the drugs. The method may be effected by one or more processing elements (e.g., processors, microcontrollers, etc.). The method includes displaying data regarding the drugs and their synergism or antagonism in a manner that is easily viewed and read and readily understood or interpreted by a user (e.g., a clinician, such as an anesthesiologist, another physician, another healthcare professional, a nurse anesthetist, another nurse, a paraprofessional, etc.).

According to one aspect, the present invention includes a method for evaluating various characteristics of a subject. These characteristics may include, but are not limited to, information about one or more of the physical characteristics of the subject, the subject's activities (e.g., physical exercise, consumption of alcohol or drugs, tobacco use or exposure to tobacco smoke, etc.), medications used by or administered to the subject, the subject's health history, and other criteria that may affect the subject's sensitivity to certain drugs. These characteristics may be used to tailor, or adjust, a drug effect model (e.g., a "population normal" model or other drug model) to the subject.

In another aspect, the present invention includes a method for modeling drugs that includes evaluating the synergism or antagonism between two or more drugs, which are collectively referred to as the "interaction" between two or more drugs that are to be used concurrently or simultaneously with one another. Such evaluation may be effected in conjunction with or separately from evaluating one or more characteristics of a subject.

Modeling in accordance with teachings of the present invention may also include identification of optimal targets, given the effects of drugs that have been or will be administered to a subject, as well as any recognized combined, or interactive effects of two or more components of the drugs. Without limiting the scope of the present invention, when the drugs are anesthetic agents, examples of optimal clinical end points include the dose of one or more types of drugs that will best achieve the desired results (e.g., sedation, analgesia, neuromuscular blocking, etc.) for a particular subject, the doses of two or more drugs that will maximize or optimize synergism therebetween, the desired wake-up time for the subject, minimal pain after wake-up, and the like. The doses may also be titrated to prevent unintended side effects (e.g., inadequate breathing by the subject, etc.). Optimal endpoints may be determined as part of the model, set by a drug administrator (e.g., a clinician, another individual who is responsible for administering drugs to a subject, or an automated device), or include some combination of modeling and administrator-input.

The interaction between two or more drugs may be evaluated in such a way that a drug administrator may readily understand the effects of a drug combination, including specific amounts of two or more drugs, on a subject. This information may be useful in dosage or titration of the drugs.

The present invention also includes apparatus that display drug models. The drug model displays are configured to provide drug administrators with a ready understanding of the interaction between two or more drugs, as well as the combined effects of the two or more drugs on a subject. Such a display may be based on a standard drug model or on a model that has been tailored to a subject, based on one or more characteristics of the subject. The displays may include two- or three-dimensional representations of the two or more drugs, as well as a representation of the combined effects of the two or more drugs on the subject. In addition, the drug model displays may be configured to show maximum and/or minimum desired effect site concentrations for a particular drug effect, indicators of events (e.g., meaningful clinical events, other responses by the subject, etc.) that may be considered in adjusting the desired maximum and/or minimum desired effect site concentrations, and other factors. These factors may be of use to a drug administrator in determining the amounts of one or more drugs a subject should receive and in optimizing the amounts of one or more drugs to be administered, as well as the manner in which one or more drugs are administered, to achieve one or more specific clinical goals.

An apparatus according to the present invention also includes input elements, including, but not limited to, user interfaces and automated input devices, by which information may be entered into a program that models the effects that a particular combination of two or more drugs may have on a subject. For example, an input element may be used to provide a processing element with data regarding the identities and dosages of one or more drugs that are to be, or have been, administered to a subject, information about a particular drug combination (e.g., synergism) administered to the subject, the effects of a particular drug combination on the subject over time, activity that may be indicative of the effects of one or more drugs on the subject, or any combination of the foregoing or other events relating to the administration of combinations of drugs to a subject.

A drug administrator may, based on a drug model that incorporates teachings of the present invention, with or without assistance from a drug model display, select a desired effect of a combination of drugs on a subject. Upon selecting the desired effect, the known synergism between the two or more drugs may be evaluated to provide specific amounts of the drugs that may predictably provide the desired effect or effects, or to titrate the drugs that are to be administered to a subject. By way of nonlimiting example, the desired effects of a combination of drugs on a subject may be selected by manipulation of a displayed model of the predicted effects of a drug combination on a "population normal" subject or a subject with one or more specified characteristics.

In addition to being useful before and during the course of drug treatment, a drug display model, display, or system may also be useful in reproducing a course of drug treatment to provide information and, possibly, insight as to the effects of the evaluated course of drug treatment. Models, displays, and systems that incorporate teachings of the present invention may also be used for instructive, or teaching, purposes.

In specific embodiments, teachings of the present invention are applicable to methods, models, and systems that may be used to predict when an anesthetized subject will wake up and, upon and after (e.g., up to about thirty minutes or more after) waking up, predict the subject's awareness of or response to pain. Such methods, models, and systems may be used in such a way as to determine optimal concentrations of a combination of anesthetics (e.g., one or more sedatives, such as propfol, seveoflurane, desflurane, isoflurane, or halothane, and one or more analgesics, such as remifentanil, fentanyl, alfentanil, or sufentanil) that will provide for minimal or an otherwise desired wake-up time, as well as concentrations of combinations of anesthetics that will minimize a subject's awareness of or response to pain without introducing unintended side-effects (e.g., inadequate breathing by the subject, etc.). The combination of anesthetic drugs evaluated and/or administered to the subject may include a sedative that will cause the subject to lose consciousness, a short-acting analgesic that blocks the subject's awareness to pain during surgery, and a long-acting analgesic that blocks the subject's awareness of pain during recovery from surgery.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which depict examples of different embodiments of various aspects of the present invention.

DETAILED DESCRIPTION

Figure 1:
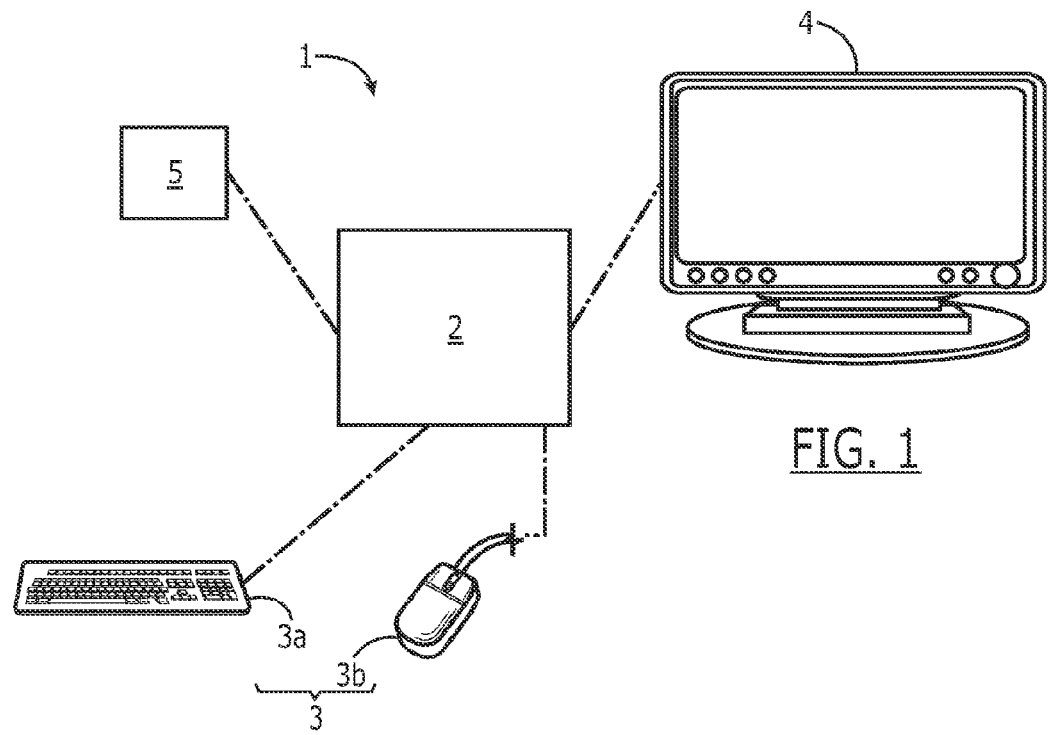
FIG. 1 is schematic representation of a system according to the present invention.

A system 1 that incorporates teachings of the present invention is schematically illustrated in FIG. 1. As shown, system 1 includes a processing element 2, and at least one input device 3, and at least one output element 4. System 1 may optionally include one or more drug delivery apparatus 5. Each input device 3, output element 4, and drug delivery apparatus 5 of system 1 may communicate with processing element 2 by means that are well known in the art.

Processing element 2 may comprise a computer, a processor, a microcontroller, or any other apparatus that may be programmed to model one or more drugs in accordance with teachings of the present invention or to output the model in accordance with teachings of the present invention. Processing element 2 includes or is configured to communicate with one or more communication elements, which are commonly referred to as "ports," to facilitate communication with other devices, such as one or more input devices 3 and one or more output elements 4.

Input device 3 may include, without limiting the scope of the present invention, input devices that are commonly associated with computers, including, without limitation, a keyboard 3a (e.g., a so-called QWERTY keyboard, a numeric keypad, etc.), a manually-manipulable element 3b (e.g., a mouse, a touch pad, a roller ball, a touch-sensitive monitor (in which case input device 3 and output element 4 could be integrated with one another), etc.), a scanning element (which may be configured to read bar codes, alpha-numeric characters, etc.), a microphone and voice-recognition software, or the like. Other types of input devices that may be used in system 1 include apparatus that are configured to automatically communicate data to processing element 2. For example, input device 3 may include drug delivery apparatus that communicate data corresponding to amounts (e.g., volumes, concentrations, weights, etc.) of drugs administered to a subject to processing element 2. As another example, input device 3 may comprise one or more monitoring devices (e.g., respiratory monitoring apparatus, pulse oximeters, and the like). Ventilators and other apparatus that are configured to communicate with computers may also be used as input devices 3 of system 1.

By way of nonlimiting example, output element 4 is depicted as a computer monitor, although output element 4 may alternatively or additionally include a printer, speakers, or other audio or visual output apparatus. As will be described in further detail hereinafter, output element 4 may be configured to communicate to a clinician or other individual a model of the concentration of one or more drugs in the body of a subject, an indication of the effectiveness of one or more drugs on the subject, or a combination of the foregoing.

Drug delivery apparatus 5 may include any suitable drug delivery device known in the art, such as infusion pumps that deliver drugs at programmed rates, bar-coded syringes combined with devices that detect the amounts of drugs administered to a subject, and the like. Drug delivery apparatus 5 may be configured to administered drugs in the form of a bolus, continuously (e.g., intravenously, as inhaled agents, etc.), or in any other fashion. Processing element 2 may communicate with drug delivery apparatus 5 in such a way as to control the amount of one or more drugs administered to a subject.

Drug Effect Modeling

In a method that incorporates teachings of the present invention, system 1 and its components may be used to model the effects of one or more drugs, as well as their interactions, on a particular subject. More specifically, the expected amounts, or levels, of one or more drugs within the body (e.g., blood, other tissues, etc.) of a subject (i.e., pharmacokinetics), as well as the effects or effect site concentrations (e.g., end tidal concentrations of inhaled anesthetic agents, cerebral concentrations of sedatives administered in any manner, other drug concentrations at the site or sites where a particular drug has a desired effect on a subject, etc.) of one or more drugs, including, but not limited to, any combined effects (e.g., synergism, antagonism, etc.) between the drugs, on the subject (i.e., pharmacodynamics) may be modeled.

Modeling may be based on a so-called "population normal patient," which is a patient of average age, height, weight, etc. of a particular sex (i.e., male or female). Data representative of "population normal patients" is available in published form from sources that are known to those of ordinary skill in the art (e.g., Schnider T W, et al., The influence of method of administration and covariates on the pharmacokinetics of propofol in adult volunteers, Anesthesiology 88: 1170-82 (1998); Minto C F, et al., Influence of age and gender on the pharmacokinetics and pharmacodynamics of remifentanil. I. Model development, Anesthesiology 86: 10-23 (1997); Plaud B, et al., Pharmacokinetics and pharmacodynamics of rocuronium at the vocal cords and the adductor pollicis in humans, Clin. Pharm. Ther., 58: 185-91 (1995); Shafer S L, et al., Pharmacokinetics of fentanyl administered by computer-controlled infusion pump, Anesthesiology 73: 1091-102 (1990)).

Alternatively, as the pharmacokinetics and pharmacodynamics of a drug or combination of drugs in the body of a particular subject may differ somewhat, or even significantly, from the pharmacokinetics and pharmacodynamics of the drug or combination of drugs in another subject, a drug modeling method according to the present invention may be adapted based on one or more particular characteristics of the subject to whom drug delivery is being modeled. Such adaptation may more closely represent the effects of drugs on a subject than conventional modeling based on the so-called "population normal" subject. Such adaptation is referred to herein as "multiple model adaptive control" or "MMAC."

MMAC may employ population normal data to generate a model based on one or more drugs, including, but not limited to, the manner of administration of the one or more drugs and the dosage of each drug. Published, population normal data may be used to provide an initial model of the expected drug levels within the body (e.g., blood, other tissues, etc.) of a subject. The model may be modified, or adapted, based on a variety of factors.

Alternatively, MMAC may be used to generate a model based upon one or more characteristics of a subject to whom one or more drugs are to be administered, as well as the effects of the one or more drugs on a subject or subjects having similar characteristics (e.g., based on a historical database of individual characteristics and corresponding drug effects).

Without limiting the scope of the present invention, factors that may be considered in generating or adapting a model (e.g., population normal, MMAC, etc.) of the effects of one or more drugs on a subject include information about the drug or drugs that are administered or are to be administered to the subject, physical information about the subject, information about the subject's lifestyle, monitored physiological parameters, response parameters, and other characteristics or parameters that define a subject's individuality.

The identity and amount of each drug that is administered to a subject may be incorporated into a model of the present invention, as may information about known, expected effects of the drugs on a population normal patient, known information about interaction of the drug with one or more other substances, such as one or more other drugs, and the like. Some sedatives are known to also have analgesic effects, and some analgesics are known to have some sedative effects. When these types of sedatives and analgesics are present in a subject's body at the same time, the overlapping sedative or analgesic effects may be additive or even synergistic.

Known interactions (e.g., synergism, antagonism, etc.) between drugs and other characteristics of different drugs may also be incorporated into a model according to the present invention. For example, it is known that, in addition to acting primarily as sedatives, some "sedative" drugs also have analgesic (i.e., pain relieving) properties. Accordingly, their analgesic properties, which may add to or act in synergy with the analgesic effects of one or more analgesic drugs that are being administered to a subject, may be incorporated into a model of the effects of one or more anesthetic drugs on a subject.

The overlapping effects of two or more different drugs, as well as differences between the drugs, may be exploited to provide a tailored, subject-specific course of treatment. For example, some sedatives are known to also have analgesic effects, and some analgesics are known to have some sedative effects. When these types of sedatives and analgesics are present in a subject's body at the same time, the overlapping sedative or analgesic effects may be additive or even synergistic. As another example, the time courses (e.g., $P_k$) of different drugs may be considered. Sedatives and analgesic agents (or "analgesics," such as opioids) have different time courses from one another due to differences in how these drugs distribute throughout the body of a subject and in how they are metabolized by a subject's body. As the time courses of these drugs are different, they are said to be "nonlinear" with respect to each other. Time courses of different drugs within a particular family (e.g., opioids) may also differ from one another, as may the pharmacokinetic profiles of different drugs. But the pharmacodynamic characteristics of different drugs within a particular family (e.g., opioids) may be similar to one another.

Physical information, or "covariates," that may define a subject's individuality and that may have an impact on how that subject reacts to a drug or group of drugs may include, without limitation, data about the drug tolerance, gender, age, weight, height, and other physical characteristics of the subject. Lifestyle information may include data regarding the subject's health, fitness, health history (e.g., renal failure, heart failure, liver failure), lifestyle, and the like.

Physiological parameters that may define a subject's individuality may include a variety of monitored conditions, such as, blood loss by the subject, blood oxygen levels ($SpO_2$), heart rate, blood pressure, processed electroencephalography signals (a measure of how sedatives influence the electrical activity in the brain), and the like. For example, an increase in a subject's heart rate or a subject's blood pressure may indicate that the subject is experiencing pain (e.g., a deviation of twenty percent (20%) or more in heart rate may be considered a clinical event). A decrease in electrical activity in a subject's brain typically indicates that the subject has become more sedate.

Response parameters, which may comprise or be closely associated with physiological parameters, include data about the subject's response to one or more drugs or to one or more stimuli, such as incisions, other invasive events, movement (e.g., shaking, jarring of the subject during surgical procedures, etc.), skin pricks, light, noise, and the like.

Data may be incorporated into the model during generation of the model, after the model has been generated, or both during and after generation of the model. The data may be incorporated on a substantially continuous basis (e.g., as it becomes available) or periodically (e.g., at one or more predetermined points in time after it becomes available). The data or information may be input or incorporated into the model manually or automatically (e.g., by drug delivery equipment, such as an infusion pump, detection of a bolus amount from a syringe, measurement of vaporized drugs (e.g., by use of infrared monitoring of the subject's breathing), etc.; by patient monitoring equipment, such as sensors for monitoring respiratory gases and flow, pulse oximeters, electrocardiograms (ECGs), electroencephalograms (EEGs), etc.; etc.). Data or information may be input into the model in an alpha-numeric format (e.g., a number on a scale that corresponds to a particular characteristic (e.g., very drug insensitive=1, population normal sensitivity=5, very drug sensitive=10; by way of numbers, letters, or terms that a computer program generating or adapting the model would "understand" or "recognize" as corresponding to a particular characteristic; etc.), by manipulation of computer-generated graphics, or in any other suitable manner.

Data and other information that may be pertinent to the effectiveness of one or more drugs with respect to a particular subject may be considered and, optionally, incorporated into the model automatically, or it may be considered by an individual, such as a clinician or other drug administrator, who may then adjust the model based on his or her understanding of or experience with how such information will influence the effectiveness of one or more drugs. As a nonlimiting example, the effects of one or more anesthetic agents, including sedatives, analgesics, and neuromuscular blocking agents, on a subject may be modeled in accordance with teachings of the present invention. In generating or adjusting the modeled effects of one or more anesthetic agents on a subject, a variety of information may be considered. For example, the subject's weight and drug, alcohol, and tobacco usage may be considered. Someone who is overweight, and uses alcohol, tobacco, and several prescription drugs, may exhibit a high tolerance to anesthesia, while a subject that is relatively lightweight and is a "chemical virgin" may be anesthetically much more sensitive. Thus, these two subjects may require significantly different dosages of anesthesia to provide substantially the same anesthetic effect.

Furthermore, by monitoring a subject as or after one or more drugs are administered to the subject, the drug administrator may adapt the model by scaling an output (e.g., displayed) effect of the one or more drugs on the subject to the subject's actual response to the one or more drugs. Continuing with the example of anesthetic drugs, a drug administrator could observe various characteristics of the subject, such as the subject's response to stimuli (e.g., incision, pin prick, shaking, etc.), then adapt the drug model accordingly.

Figure 2:
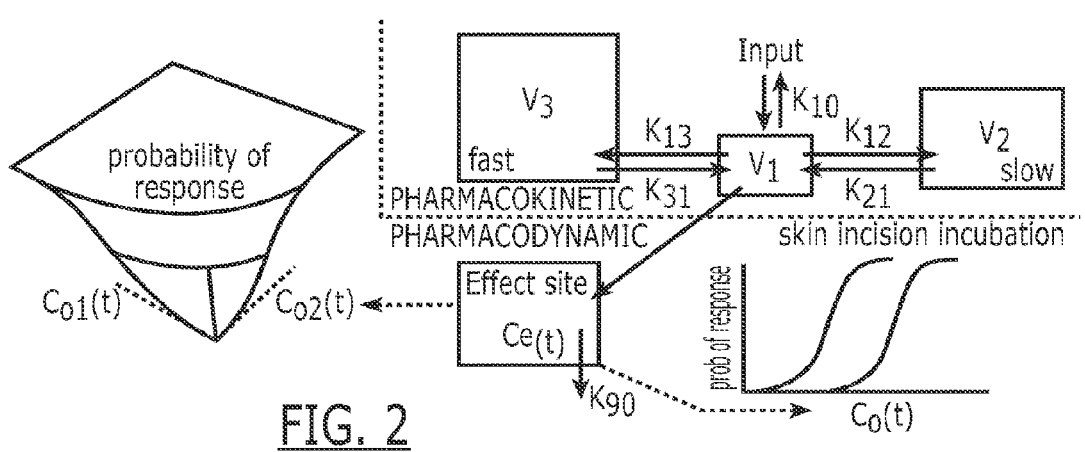
FIG. 2 is a schematic representation of an example of a $P_k$-$P_d$ model that incorporates teachings of the present invention.

In FIG. 2, a schematic representation of a $P_k$-$P_d$ model that incorporates teachings of the present invention is provided. The depicted $P_k$-$P_d$ model includes three compartments for describing time course of drug concentration. The pharmacokinetics ($P_k$) and pharmacodynamics ($P_d$) are linked by predicting drug concentrations in the effect site. The relationship between effect site concentration over time, ce(t), and drug effect (e.g., $P_d$) is characterized by a sigmoidal concentration-response model, indicating the probability of response from 0% to 100%.

In addition, or as an alternative to modeling the effects of one or more specific drugs on a subject based on one or more of individual characteristics of the subject, the amount of each drug administered, and the manner in which each drug is administered, the present invention includes methods from providing a user with information on a predicted, optimal protocol for treating a subject to achieve a particular result. Without limiting the scope of the present invention, such a method includes identifying a desired effect, or result, identifying one or more individual characteristics of the subject, and modeling a drug or drug combination and amount of each drug to be administered to the subject to best achieve the desired result (e.g., with the greatest efficiency, with a maximized synergistic effect, with a maximized therapeutic effect, with the fewest undesirable side effects, etc.) and, optionally, determining a mode of administration that will achieve the desired result. Such a method may include consideration of the potential negative effects of a drug or drug combination on a subject, as well as the potential negative effects of excessive dosages of the one or more drugs. In addition, such a method may be useful for minimizing or optimizing the amount of each drug administered to the subject, which may result in cost savings, as well as other efficiencies (e.g., reduce operating room or recovery time when the drug or drugs are anesthetic agents).

With returned reference to FIG. 1, a model incorporating teachings of the present invention may be generated by processing element 2 of system 1, with data and other information being input into processing element 2 by way of input device 3.

Drug Effect Display

Once the model has been generated, processing element 2 may cause one or more output elements 4 of system 1 to display the model, or portions thereof. Such a display may provide a viewer with a ready understanding of the effects of the one or more drugs on a subject. Examples of displays that incorporate teachings of the present invention are shown in FIGS. 3 through 6.

Figure 3:
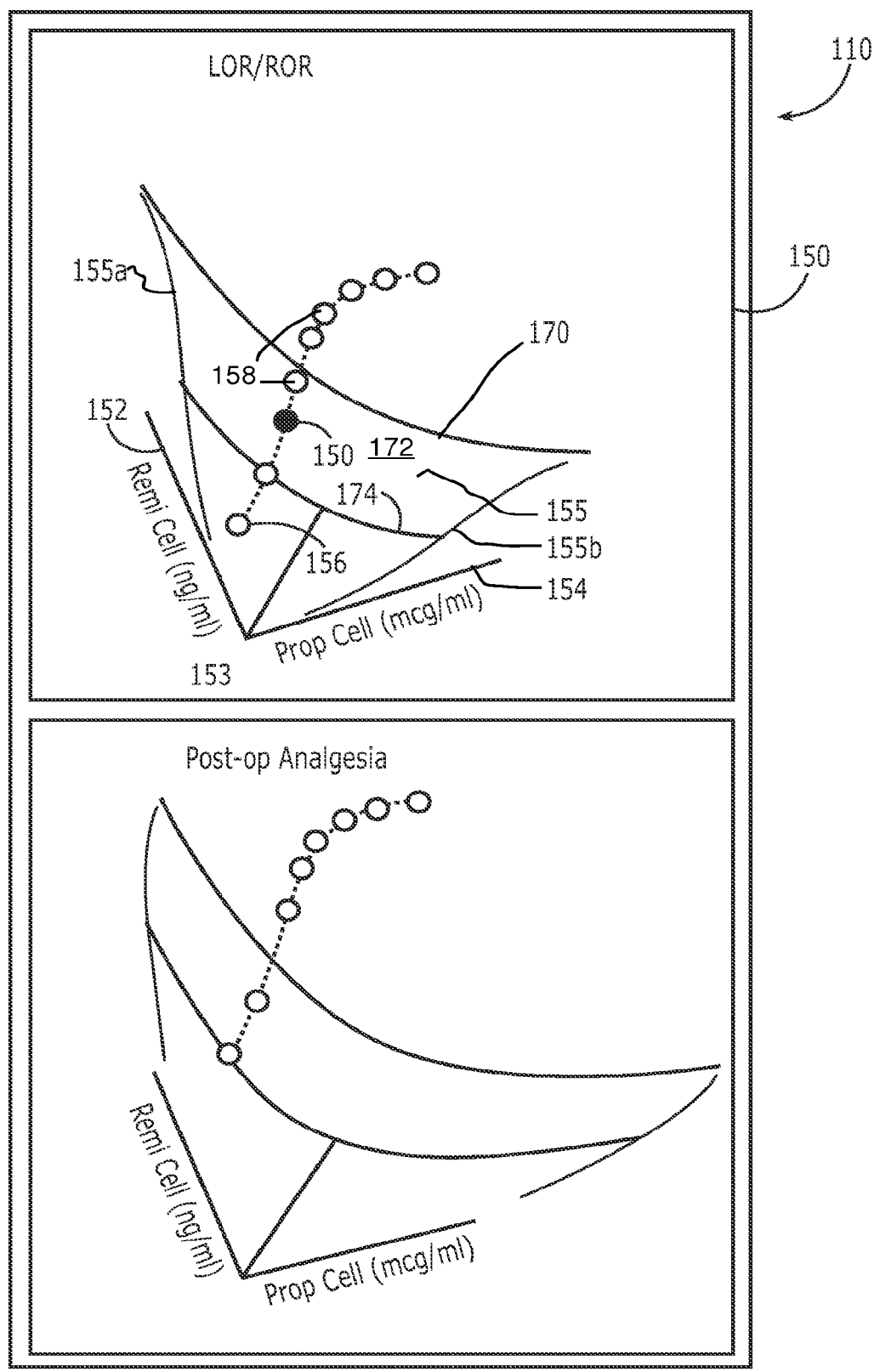
FIG. 3 depicts various features of a three-dimensional display that incorporates teachings of the present invention.

With reference to FIG. 3, an example of a display 110 that includes a three-dimensional graph 150 that incorporates teachings of the present invention is shown. Graph 150 includes two discrete axes 152 and 154 that extend in different directions from an origin 153. Axes 152 and 154 represent amounts (e.g., $P_d$) of two drugs or two types of drugs, with the amount of each drug or drug type being zero at origin 153 and increasing along its corresponding axis 152, 154 with increased distances from origin 153.

Graph 150 also includes a surface 155. Surface 155 originates at axes 152 and 154 and extends in a direction oriented transverse to a plane in which axes 152 and 154 are located, or generally along a z-axis. Surface 155 may be bounded by edges 155a and 155b. Surface 155 represents all of the different possible combinations of drug concentrations.

Time may be represented by points on surface 155. As illustrated, the $P_d$ of one or more drugs are represented at point 157, with the $P_d$ at past times being represented by points 156, and the $P_d$ at future times represented by points 158. Optionally, sequential points 156, 157, 158 may be connected by a curve, or line, to provide 2 user with a readily identifiable indication of their relationship to one another. Sequential points 156, 157, 158 may represent equal intervals of time (e.g., one minute, two minutes, five minutes, etc.), although they may not be spaced equal distances apart from one another.

Curves 170, 174, or lines, on surface 155 represent specific probabilities that a drug or combination of drugs will have a particular effect (e.g., a sedative effect, an analgesic effect, etc.) on a subject. Beyond an uppermost curve 170, 174, an orientation of surface 155 may change. For example, the portion of surface 155 beyond curve 170, 174 may be oriented substantially horizontally, rather than substantially vertically.

In the depicted example, graph 150 includes two curves 170 and 174, with the lower curve 170 representing a 50% probability (EC50) that one or more drugs will have a desired effect, while the upper curve 174 represents a 95% probability (EC95) that one or more drugs will have the desired effect. Point 157 is located between curve 170 and 174, indicating that a current modeled $P_d$ of one or more drugs has somewhere between a 50% probability and a 95% probability of providing the desired effect.

As graph 150 illustrates the $P_d$ of two drugs or two types, graph 150 may be used to identify a variety of combinations of amounts of the two drugs or drug types that will provide a desired effect.

Other factors, such as indicators of the amount of and manner in which each drug is administered, events that occur during the course of administration or treatment, and the like, may also be included in a three-dimensional graph (e.g., graph 150) of the present invention.

The surfaces (e.g., surface 155) of three-dimensional pharmacodynamic drug interaction models provide information that enhances the clinical applicability of the models. This is because the surfaces mathematically characterize the entire spectrum of drug-drug interaction, ranging from low to high concentrations for both drugs of interest, rather than the single slice of any possible drug combination provided with conventional, standard isobolographic drug interaction analyses. As shown in the example of FIG. 3, the response surface may bow towards the origin to indicate synergism between two or more drugs used in combination. In addition, the isoboles, which are lines that laterally, or horizontally, traverse the surface, indicate all concentration pairs that achieve a particular probability of response. At any point along an intermediate location of a particular isobole (e.g., curve 170 or 174), which represents that a combination of drugs is being administered to a subject, lower concentrations of both drugs are required to achieve the same effect as either of the drugs alone, as represented at the location where the ends of that isobole intersect each axis 152, 154 of graph 150. The response surface 155 provides a rich characterization of drug-drug interaction, with great potential for clinical application, because it predicts the interaction over a full range of concentrations employed by a clinician.

Figure 4:
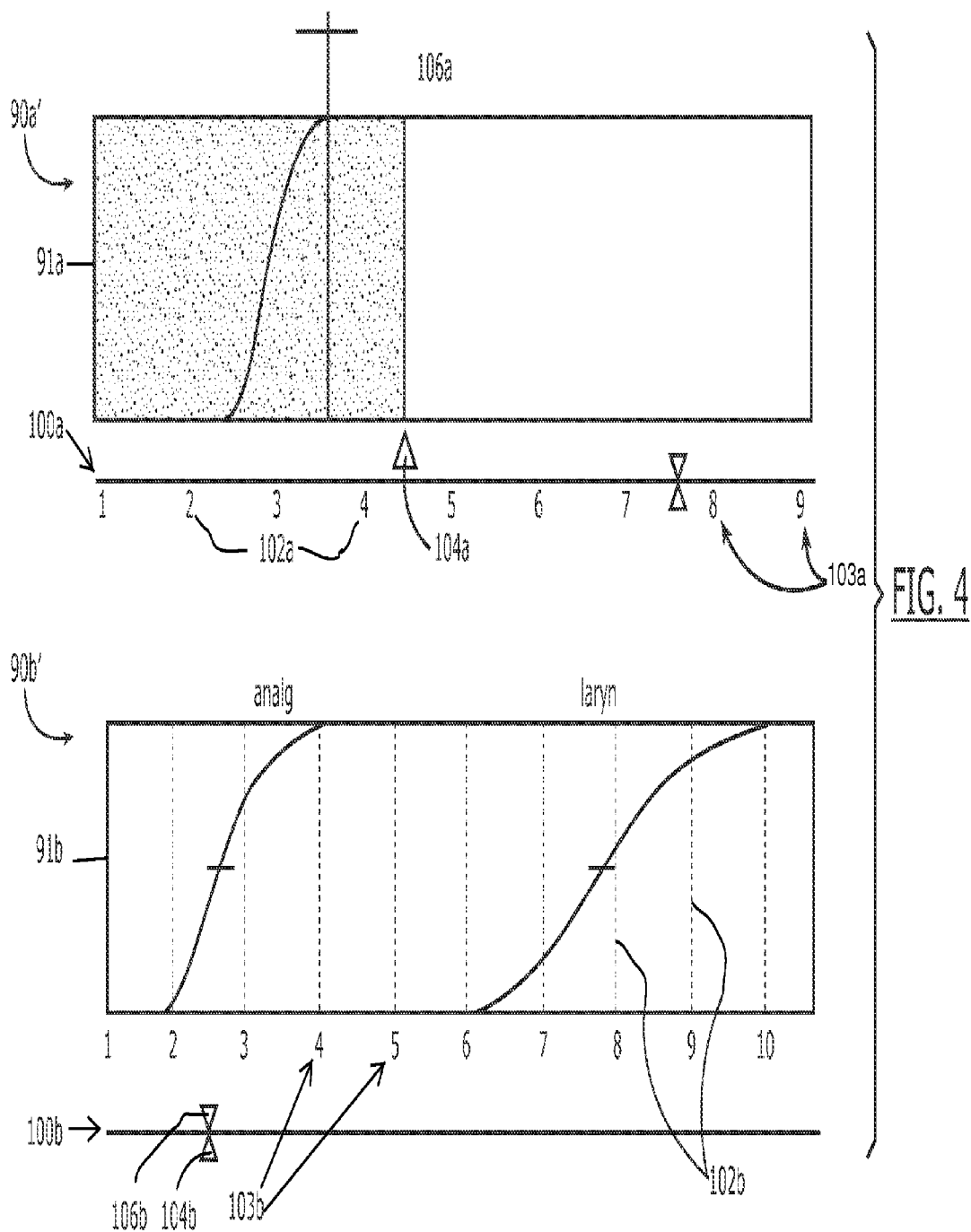
FIGS. 4 through 6 depict various features of two-dimensional displays that incorporate teachings of the present invention.

With continued reference to FIG. 3 and with reference to FIG. 4, data from a three-dimensional graph (e.g., graph 150) may be converted to a readily understood or interpreted two-dimensional format. For example, edges 155a and 155b of surface 155 of graph 150 (FIG. 5) may represent a minimum desired effect and a maximum desired effect of a drug or combination of drugs. When the desired effect is sedation, edges 155a and 155b may respectively represent the effectiveness of one or more drugs in providing adequate skin closure analgesia and laryngoscopy analgesia. As the curves of edges 155a and 155b may be somewhat difficult to interpret or quantify on a three-dimensional graph, they may be more readily understood in the context of a two-dimensional graph, such as that shown in FIG. 4. In the illustrated example, curve 92W corresponds to edge 155a, while curve 92b" corresponds to edge 155b.

With returned reference to FIG. 3, graph 150 may include interactive features, such as those described in reference to display 10' and graphs 90a' and 90b', which provide for user manipulation which may, in turn, be used to adjust or modify a model represented by graph 150 or the amount of one or more drugs administered to a subject. In addition, surface 155 of graph 150 may be shifted to account for a subject's sensitivity to one or more drugs. For example, surface 155 may be shifted increasingly outward if the subject is more sensitive to the effects of one or more drugs. Conversely, surface 155 may be shifted increasingly inward if the subject is less sensitive to the effects of one or more drugs. The direction of the shift relative to origin 153 and, thus, the distance of the shift away from each axis 152, 154, depends, of course, upon the subject's sensitivity to each drug or drug type represented by axes 152 an 154 of graph 150.

Other manipulations may be made by a user (e.g., with an input device 3; FIG. 1) to graph 150 to cause a processing element 2 of system 1 to control a drug delivery apparatus 5 in such a way as to vary the amounts of one or more drugs that are administered to a subject.

As three-dimensional displays may not intuitively provide a healthcare provider (e.g., a physician) with a ready understanding of the interaction between two or more drugs, easy-to-understand two-dimensional models have been developed to provide healthcare providers with readily interpretable information about interactions, including synergies, between drugs that are concurrently administered or that are present within a subject's body at the same time.

Figure 5:
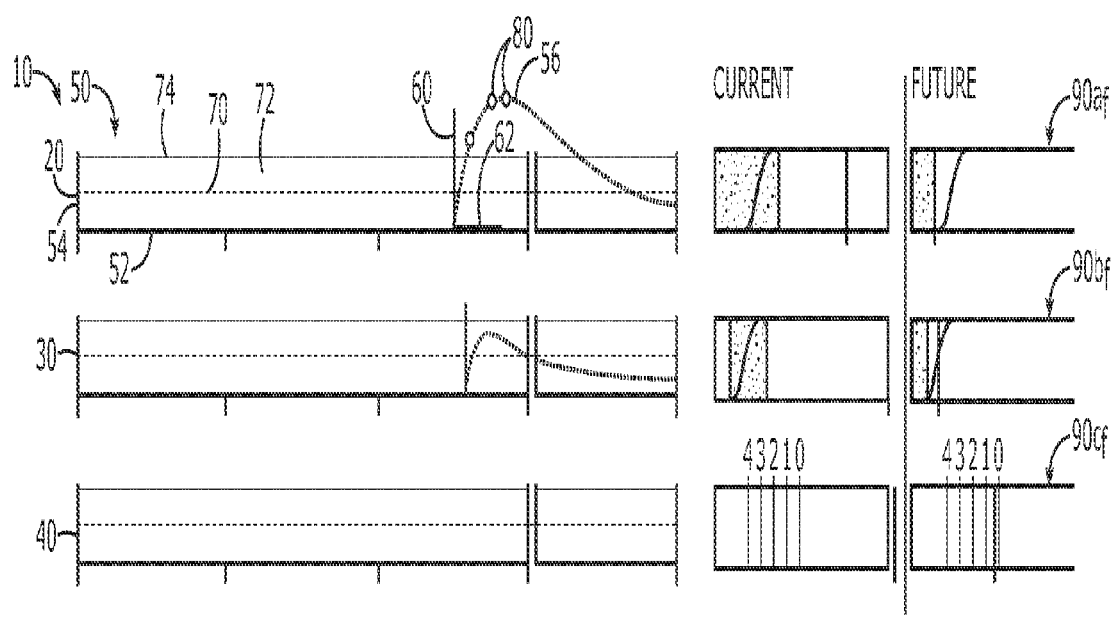

An example of a two-dimensional display 10 according to the present invention is provided in FIG. 5. The illustrated example of display 10 includes three sections 20, 30, and 40, or tiers. Although three sections are shown, a display that incorporates teachings of the present invention may include one section or more. Each section 20, 30, 40 corresponds to a particular drug effect. By way of nonlimiting example, display 10 may depict an anesthesia model, which may include three components: a sedative component, which is represented at section 20; a neuromuscular blockade (or "muscle relaxant") component, which corresponds to section 30; and an analgesia component, which is represented by section 40. The effects of one or more drugs may be represented by each section 20, 30, 40 of display 10. One or more drugs may be represented in multiple sections 20, 30, 40 of display 10.

In the depicted example, each section 20, 30, 40 of display 10 comprises a graph 50 with a horizontally oriented k-axis 52 and a vertically oriented y-axis 54. Without limiting the scope of the present invention, x-axis 52 may represent time, while y-axis 54 may represent the concentration of a drug or its anticipated, or modeled, effect on a subject. Accordingly, data of the modeled concentration or effect of each drug may be shown at one or more points in time. With respect to an example of the manner in which time may be represented by graph 50, past times may appear at or near the left of x-axis 52 of graph 50, the current time may be represented near the center of x-axis 52, and future times may appear at the right of x-axis 52.

As a nonlimiting example, the data may be depicted, over a modeled period of time, as a single-drug effect line 56 that extends somewhat horizontally along graph 50. As the concentration or effect of the drug may be affected by one or more other factors, such as another drug, the combined effect (e.g., synergism, competition, antagonism, etc.) of the drug and one or more other factors may also be shown on graph 50, such as by a combined-drug effect line 58 or another combined effect indicator.

In addition to including features that depict the concentration or effect of one or more drugs, as well as the combined effect of the drug and one or more other factors, graph 50 may include one or more other elements.

For example, and without limiting the scope of the present invention, graph 50 may include one or more drug administration indicators 60, 62. Each drug administration indicator may be configured to provide a viewer of graph 50 with an understanding of the administration of one or more drugs, including, but not limited to, the identity of each drug that was, is being, or will be administered to a subject, the manner in which the one or more drugs were, are, or will be administered to the subject, the amount of each drug that has been, is being, or will be administered to the subject, and the like.

Continuing with the depicted example, drug administration indicator 60 is a generally vertically oriented bar positioned over a single point in time along x-axis 52. As such, drug administration indicator 60 represents a bolus administration of a drug. Drug administration indicator 60 has a height that corresponds to a dose of the drug that was administered to the subject, which dose may or may not be normalized. If the dose of the drug was not normalized, a width of drug administration indicator 60 may correspond to a concentration or recommended dose of the drug. A color of drug administration indicator 60, or a tag associated therewith, may correspond to an identity of the drug administered to the subject.

Drug administration indicator 62 is oriented somewhat horizontally, indicating that it represents a drug that is administered for a period of time by infusion. A vertical location of drug administration indicator 62 on graph 50 may correspond to the amount of the drug administered to the subject. If the amount of the drug administered is not normalized, a thickness of drug administration indicator 62 may correspond to a concentration or recommended dose of the drug. The identity of the drug represented by drug administration indicator 62 may be represented by a color of drug administration indicator 62 or a tag associated therewith.

Although not shown, a display that incorporates teachings of the present invention may be configured to depict drug administration by other means, including, but not limited to, intramuscular, transmucousal, transcutaneous, oral, and inhaled modes of administration.

Graph 50 may also include one or more probability indicators. As an example, graph 50 may include a generally horizontally extending line, or wire 70, 74, that represents a particular concentration of one or more drugs. Each wire 70, 74 may stand alone or, as depicted, comprise an upper or lower limit of a band 72, which may comprise a "therapy window," that represents a range of concentrations of the one or more drugs (e.g., in a therapy window, etc.) may be within a desired range of effectiveness (e.g., have a desired pharmacodynamic effect). The relative position of a point on a single-drug effect line 56 relative to wires 70, 74 or band 72 provides a user with an indicator of the modeled probability that the represented drug will have a desired effect on the subject at a particular point in time. Likewise, the position of a point on combined drug-effect line 58 relative to wires 70, 74 or band 72 provides a user with an indicator of the modeled probability that the represented combination of drugs will have a desired effect on the subject at a particular point in time. In addition to one or more wires 70, 74, a graph 50 that incorporates teachings of the present invention may include more than one band 72, which may represent a "therapy window," within which one or more drugs will have a desired effect site concentration and, within the desired range of probabilities, achieve a desired clinical outcome, or have a desired effectiveness.

Without limiting the scope of the present invention, wire 70 may represent a drug concentration at which there is a ninety-five percent (95%) probability (EC95) that a particular drug or combination of a drug and other factors (e.g., one or more other drugs) will have a desired effect on a subject or that the amount of one or more administered drugs will have the desired effect on a specific part (e.g., 95%) of the general population. Wire 70 forms the upper boundary of band 72, the lower boundary of which is defined by a wire 74 that corresponds to a fifty percent (50%) probability (EC50) that the drug or a combination of the drug and one or more other factors will have the desired effect on the subject or on a specific part (e.g., 50%) of the general population.

As discussed elsewhere herein, the vertical position of each wire 70, 74 or band 72 may shift automatically or be shifted by user input. Such shifting may occur, for example, if one or more factors indicate that the effectiveness of a drug or any other factor is different than originally anticipated, or modeled. Indicators of the effectiveness of a drug include, but are not limited to, a subject's responsiveness to the drug or, when the drug is an anesthetic agent, the subject's responsiveness to various stimuli.

A graph (e.g., graph 50) that incorporates teachings of the present invention may include one or more event indicators 80, such as the depicted symbols (e.g., diamonds, squares, circles, arrowheads, etc.), that indicate points in time (e.g., relative to x-axis 52) at which various events that may affect the effectiveness of one or more drugs on the subject. By way of nonlimiting example, event indicators 80 may correspond to monitored physiological parameters or response parameters. Event indicators 80 may be automatically inserted into graph 50 by a processing element 2 (FIG. 1) that generates graph 50, or under user control. Examples of events that may be represented by event indicators 80 include physiologic events (e.g., an increase or decrease in heart rate by a threshold value, a change in blood oxygen levels ($SpO_2$), a change in blood pressure, a change in enthropy (which is a measure of electrical activity in a subject's brain), etc.), an event conducted by a clinician to determine effectiveness of the drug (e.g., a pin prick test, evaluation of the pupils of a subject's eyes, etc.), and the like.

Data that corresponds to one or more event indicators 80 may be pertinent to the generation or adjustment of a model in accordance with teachings of the present invention. Accordingly, processing element 2 (FIG. 1) may recognize data associated with one or more event indicators 80 as or after such event indicators 80 are generated or "placed" on display 10. Such "recognition" may occur automatically, by surveying the display occasionally (e.g., at predetermined intervals), or by appropriate user input. Processing element 2 (FIG. 1) may then incorporate such data into the model, adjust the model if necessary, and cause output element(s) 4 to display the adjusted model or adjust the previously displayed model accordingly. Additionally, an output may be provided to indicate to a clinician whether or not an additional or increased (or decreased) amount of one or more drugs should be administered to the subject in response to one or more events.

Figure 6:
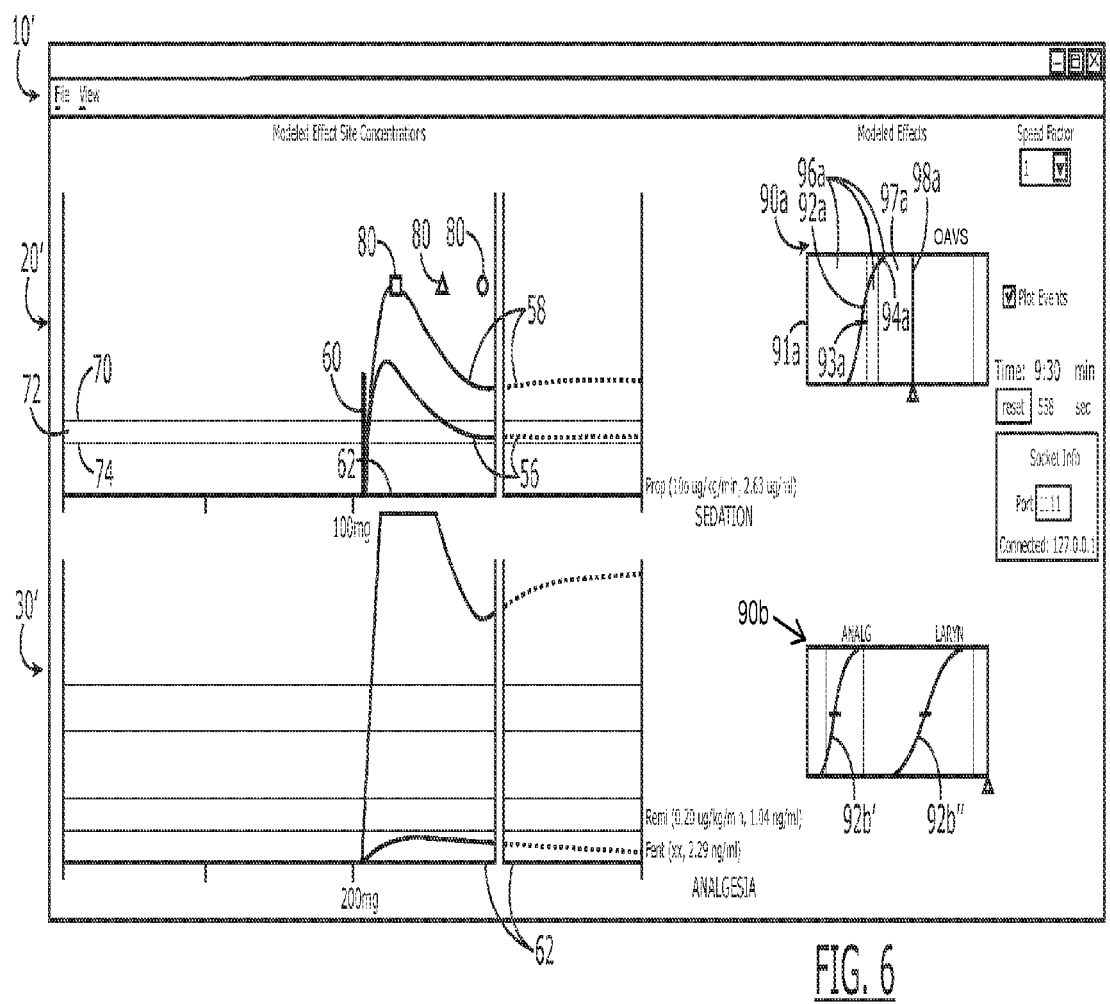

Turning now to FIG. 6, another example of a two-dimensional display 10' according to the present invention is depicted. As illustrated, display 10' includes two sections 20' and 30', although displays with a single section and displays with more than two sections are also within the scope of the present invention. Like display 10 (FIG. 2), each section 20', 30' of display 10' may include a graph 50 with an x-axis 52 and a y-axis 54, drug effect lines 56 and 58 that illustrate modeled ($P_k$) of one or more of past, present, and future (e.g., ten minutes into the future) effect site concentrations, drug administration indicators 60 and 62 that serve as indicators of dosing history, and one or more wires 70, 74 or bands 72 that provide an indication as to a probability that a particular drug is having a desired effect on a subject. Event indicators 80 may also be included on each graph 50 of display 10'.

Additionally, display 10' includes concentration-effect graphs 90a and 90b (collectively "concentration-effect graphs 90") provide $P_d$ and $P_k$ models of one or more administered drugs (in this example, a sedative (propofol) and a pair of analgesics (remifentanil and fentanyl), although concentration-effect graphs may show a number of other drug effects, including, without limitation, the effects of one or more drugs on blood pressure, arrhythmia, cardiac contractility, peripheral vascular resistance, airway resistance, etc.). As shown, concentration-effect graph 90a depicts the modeled sedative effects of two or more drugs on a subject, while graph 90b depicts the modeled analgesic effects of a combination of two or more drugs on the subject.

More specifically, graph 90a is a horizontal bar graph that, from left to right, shows the "current," modeled $P_d$ of one or more drugs (in this case, a sedative effect of the one or more drugs), with no effect being represented as the left-most edge 91a of graph 90a. Of course, a concentration-effect graph may model projected (i.e., future) effects of one or more drugs at a particular point in time (e.g., ten minutes in the future). Graph 90a includes a curve 92a, as well as one or more $P_d$ bands 96a that correspond to one or more administered drugs, an optional combined effect band 97a, and a total effect bar 98a.

In the illustrated example, curve 92a is a somewhat vertically extending sigmoidal curve. Curve 92a demonstrates the probability that one or more drugs will have the desired effect on a subject (in this case, a sedative effect). The small horizontal line 93a at the center of curve 92a represents the $P_d$ of one or more administered drugs that is predicted to have a 50% probability of providing the desired effect. The location of the top end 94a of curve 92a represents the $P_d$ of one or more administered drugs that is predicted to have particularly high probability (e.g., 95%) of providing the desired effect.

In the illustrated example of graph 90a, three $P_d$ bands 96a extend, in sequence, from left-moist edge 91a of graph 90a. $P_d$ bands 96a represent the $P_d$s of three drugs administered to a modeled subject (in this case, propofol, fentanyl, and remifentanil). An additional effect band 97a, which is positioned to the right of and adjacent to $P_d$ bands 96a, represents the additional sedative $P_d$ that occurs due to synergism between the represented drugs.

Total effect bar 98a is positioned at the right edge of additional effect band 97a, and represents the modeled, combined $P_d$ of drugs that have been administered to the subject. As shown, total effect bar 98a is positioned to the right of top end 94a of curve 92a, indicating to a user that the drug or drugs that have been administered to the subject will have a probability of effectiveness that exceeds the uppermost probability represented by top end 94a (e.g., a 95% of providing the desired effect, such as losing or recovering from responsiveness due to sedation). In this case, it might be desirable for a user to facilitate a reduction in the amount or amounts of one or more drugs administered to the subject, as the drug or drugs are modeled to have a more than adequate effect. Of course, if total effect bar 98a were positioned along curve 92a or to the left of curve 92a (the bottom end 95a of which may represent a low probability, such as 5%, that the drug will have the desired effect on the subject), a user would be provided with an indication that it might be desirable to increase an amount of one or more drugs administered to the subject.

Graph 90b, which includes the same features as graph 90a, includes two curves 92b' and 92b" that represent different effect thresholds. In the depicted example, graph 90b represents the "current," modeled analgesic effects of one or more drugs on a subject. The curve 92b' at the left of graph 90b may represent a probability that the one or more drugs will have a sufficient analgesic effect to relieve the subject's light pain (e.g., post-operative pain or skin closure), while the curve 92b" at the right of graph 90b may represent a probability that the one or more drugs will have a sufficient analgesic effect to prevent the subject from feeling pain during laryngoscopy and intubation. The effects displayed in graph 90b or any other similar graph that incorporates teachings of the present invention may reflect the effects of one or more drugs on measurable clinical endpoints, such as a level of pain (e.g., algometry (a measure that corresponds to post-operative pain that may be evaluated by impacting a piston on a subject's shin), tetanic stimulus (a measure of skin incision pain that may be measured by administration of electrical shock and counting the number of muscle (e.g., thumb, finger, etc.) twitches), etc.), a level of sedation (based on, e.g., an observer's assessment of alertness/sedation, or OAA/S), loss of consciousness, or the like.

Other examples of graphs 90a' and 90b' that may be included in a display according to the present invention are shown in FIG. 4. In addition to including at least some features described above in reference to graphs 90a and 90b, each graph 90a', 90b' includes a sensitivity indicator 100a, 100b.

In the illustrated example, each sensitivity indicator 100a, 100b includes gradations 102a, 102b associated with a length 99 of graph 90a', 90b', as well as slider 104a, 104b with a sensitivity indicator 106a, 106b, depicted as a having a bow-tie shape, that may be "moved" along length 99 of graph 90a', 90b' by a user.

In addition, numbers 103a, 103b may be associated with gradations 102a, 102b to provide an indicator, which may or may not be at least somewhat standardized, of a subject's actual or predicted, perceived sensitivity to one or more drugs. As depicted, numbers 103a, 103b increase (e.g., "1") from left edge 91a, 91b of graph 90a, 90b to (e.g., "9" or "10") at the right edge of graph 90a, 90b. By way of nonlimiting example, the number "1", at the left of slider 104a, 104b may represent a highest level of drug sensitivity. The number "5", near the center of slider 104a, 104b, may represent the sensitivity of a "population normal" subject. The highest number of the scale (e.g., "10") may represent complete insensitivity to a drug.

As shown in FIG. 4, the sensitivity indicator 106a associated with graph 90a' is positioned at a location that represents a subject's perceived sensitivity to at least one sedative. In the depicted example, sensitivity indicator 106a is positioned along slider 104a between "7" and "8", indicating that the subject is extremely insensitive to the represented drug or drug effect. Sensitivity indicator 106b, which is associated with graph 90b', is positioned at a location indicative of the subject's perceived sensitivity to at least one analgesic. As illustrated, the positioning of sensitivity indicator 106b between "2" and "3" on slider 104b, indicates that the subject is very sensitive to analgesics.

Movement of a sensitivity indicator 106a, 106b (e.g., with an input device 3 (FIG. 1) may be communicated to processing element 2 (FIG. 1), which may, based on such movement, generate or adjust a model or vary the amount of one or more drugs administered to the subject.

Other features of a display that incorporates teachings of the present invention (e.g., lines 56 and 58, indicators 60 and 62, wires 70 and 74, effect bands 96 and 97, total effect bar 98, etc.; see, e.g., FIGS. 4 through 6) may also be adjusted by a user. Such adjustment may, in turn, be "recognized" or processed by processing element 2 in a manner known in the art, which may, in turn, vary the manner in which drugs are administered by drug delivery apparatus 5.

When an optimal course of treatment is modeled, a display according to the present invention may include information as to the type and amount of each drug to be administered to a particular subject and, optionally, the mode by which the drug or drugs are to be administered.

A display of the present invention may be provided on site, or sent remotely to a clinician who is at a different location than either the subject to whom drug delivery is being modeled or the drug modeling system.

Use of Display to Adjust or Modify Model

With returned reference to FIG. 1, as has been noted, various elements of a display that incorporates teachings of the present invention may be manipulated automatically or by a user (e.g., with an input device 3 of system 1) in response to predictions of a model. Such manipulation may be effected or evaluated, or processed, by processing element 2, which may alter or modify a drug model, as well as a display of the drug model, as output by one or more output elements 4 of system 1.

As indicated, one example of the manner in which a display may be manipulated to adjust or modify a drug model includes movement of an indicator of a probability that a drug or combination of drugs will have a desired effect on a subject. In a two-dimensional display, such as those shown in FIGS. 4 through 6, a single-drug effect curve 56 or a combined-drug effect curve 58 may be adjusted upward of the modeled drug or drugs have a greater-than-expected effect on the subject or, if the modeled drug or drugs have a less-than-expected effect on the subject, curve 56 or 58 may be adjusted downward.

Alternatively, or in addition, one or more effectiveness indicators, such as a wire 70, 74 or band 72, may be adjusted downward if the modeled drug or drugs have a greater-than-expected effect on the subject. Alternatively, if the drug or drugs have a less-than-expected effect on the subject, the indicator or indicators may be shifted upward.

In addition, various features of a display may be manipulated in such a way as to vary the amount or amounts of one or more drugs that are administered to a subject.

Similar adjustments may be made in a three-dimensional display, such as that depicted in FIG. 5 (e.g., by movement of surface 155 of graph 150), as described previously in reference to FIG. 5. In particular, drug delivery may be optimized according to interactions (e.g., synergism, antagonism, etc.) between drugs. Surface 155 of graph 150 readily and intuitively indicates how the drugs can be administered in different combinations to achieve the same effect. By way of nonlimiting example, surface 155 of graph 150 shows that a low dose of remifentanil and a high dose of propofol may achieve the same effect on a subject as a moderate dose of remifentanil and moderate dose of propofol. The "shape" of surface 155 may be used to minimize the amounts of drugs that are administered, maximize drug-drug synergism, optimize wake-up time while preventing the subject from feeling pain while waking up and following wake-up, and facilitate optimal recovery of responsiveness, while maintaining adequate post-operative analgesic levels and preventing unintended side effects (e.g., inadequate breathing by the subject, etc.).

In addition, as noted in reference to FIG. 5, data (e.g., information about certain events) may be input during the course of treatment. Consideration of such data may be useful in determining whether the drug or drugs that have been administered are having the desired effect or effects and, if necessary, responsive adjustments in drug administration may be made. This data may also be useful for altering the way in which modeling of the drug or drugs administered to a subject is effected, as well as for identifying the potential need for modifying the manner in which modeling is effected for the general, "normal" population or for one or more segments of a population.

Use of the Model, Display, and System

Models, displays, and systems that incorporate teachings of the present invention may be used for a variety of purposes.

For example, a model, display, or system of the present invention may be used as an anticipatory tool to provide a user (e.g., an anesthetist/anesthesiologist) with an idea of how one or more drugs (e.g., anesthesia) will affect a certain subject before the drug or drugs are actually administered to the subject. For example, a model may be generated and, optionally, displayed to develop or plan a course of treatment that is anticipated to provide desired results (e.g., efficiency, effectiveness, safety, etc.).

Alternatively, a model, display, or system that incorporates teachings of the present invention may be used as one or more drugs are administered to a subject to provide information that may be useful in altering or modifying a course of treatment. Models, including predictive or forward-looking portions thereof, may be displayed in real-time or sped up to show the likely effects that will happen at some point in the future. For example, a physician may "fast forward" the model to view near-future and future model predictions to titrate drug administration to provide a desired near-future or future result. As a more specific example, an anesthesiologist may use near-future or future model predictions to titrate anesthesia administration in such a way as to facilitate responsiveness of a subject at a desired point in time, while maintaining adequate analgesia for post-operative pain. Examples of displays that depict such "fast forwarding" are represented at the right sides of each graph 20, 30, 40 shown in FIG. 2, by the right-most graphs $90a.sub.f$, $90b.sub.f$, and $90c.sub.f$ shown in FIG. 5, and at the right sides of the graphs 20' and 30' shown in FIG. 6.

A drug display model, display, or system may also be useful in reproducing a course of drug treatment to provide information and, possibly, insight as to the effects of the evaluated course of drug treatment.

Teachings of the present invention may be also be used to teach individuals who are training to administer or monitor administration of drugs. For example, a model, display, or system of the present invention may be used to determine the possible effect or effects of a student's or resident's proposed course of drug treatment. As another example, a model, display, or system of the present invention may be used in evaluating decision making by a nurse or other clinician in training.

In a further example, a model, display, or system according to the present invention may be used to collect data, including actual or perceived effects of one or more drugs, that may subsequently be used to refine the manner in which modeling for a subject with a particular, individual set of characteristics is effected. Collected data may be incorporated into a centralized database, from which it may be used to modify the manner in which drug modeling is effected for the patient normal population or one or more segments thereof (e.g., subjects having certain physical characteristics).

In addition, a model, display, or system that incorporates teachings of the present invention may be used in a variety of environments.

As an example, a model, display, or system of the present invention may be used by anesthesiologists in operating room environments, as well as in other environments (e.g., medical and dental clinics, etc.) where a subject is sedated, to optimize drug (e.g., anesthesia) delivery. By monitoring the presentation of drug history (boluses, infusion rates, anesthetic gas MAC), predicted drug levels, optimal drug synergism, and drug reversal agents, an anesthesiologist may make fewer mistakes, reduce instances of inadequate analgesia, increase safety of the subject during the procedure, control the hemodynamics of an anesthetized subject, provide faster wake-up times without compromising analgesia or causing unintended side effects (e.g., inadequate breathing by the subject, etc.), reduce amounts of anesthesia administered to a subject, and reduce instances of premature release of a subject from a medical facility. Possible results of such use include, but are not limited to, increased patient sensitivity to anesthesia and significant reduction in costs associated with anesthesia.

A model, display, or system of the present invention may also be used in an intensive or critical care setting. In particular, such a model, display, or system may be used to provide a nurse or other clinician with sufficient information to effectively monitor intravenous drug doses and effects. The model, display, or system may provide the nurse or other clinician with an intuitive understanding of the effects of one or more drugs on a subject (e.g., of the complex relationships of pharmacology, interactions between multiple drugs, etc.) and, thus, may reduce the number of mistakes made in intensive and critical care settings.

In addition, drug delivery may be driven by a model that incorporates teachings of the present invention. The $P.sub.d$ of one or more drugs, as well as interactions between drugs, may be used to define the clinical endpoints that are to be achieved and, thus, to deliver one or more drugs in a way that will achieve the desired endpoints.

Example 1

Anesthesia is provided as an example of a drug modeling and display in accordance with teachings of the present invention.

A course of anesthesia may be initiated by administering a bolus or an infusion of sedative. The model for that particular sedative identifies a point in time in the future by which an additional bolus or infusion of that sedative, another sedative, or an analgesic that synergistically interacts with the sedative(s) should begin. Presentation of the pharmacokinetic and pharmaocodynamic models in accordance with teachings of the present invention may facilitate optimization of titration of multiple drugs (e.g., to achieve a rapid and comfortable state of adequate sedation).

In generating a model, effect of each administered drug on a subject is based, at least in part, upon the type of drug or drugs administered to the subject, the amount of each drug administered to the subject, known drug-drug interactions, and characteristics of the subject (e.g., the population normal subject, a modeled subject having one or more characteristics in common with the subject to which drugs are being administered, etc.). Other factors, such as the manner in which the drug is administered, parameters that may indicate the effects of the drug or drugs on the subject, the subject's responsiveness to stimuli, and the like, may also be considered in generating the model.

With returned reference to FIG. 6, the modeled effect of each drug on a subject at a particular point in time may be represented by one or more lines (e.g., single-drug effect line 56, combined-drug effect line 58) that extend substantially parallel to x-axis 52 of graph 50. The location of each single-drug effect line 56 and combined-drug effect line 58 at a particular point in time relative to x-axis 52 corresponds to the modeled effect, or $P.sub.d$, of one or more administered drugs in the body of the subject at that point in time, which effect corresponds to along y-axis 54 position of a particular point of that line 56, 58, based upon the amount of the drug that was previously or is continuously being administered to the subject.

Wires 70 and 74, as well as band 72 therebetween, provide reference points as to a target concentration for a single drug (single-drug effect line 56) or a combination of drugs. Specifically, wires 70 and 74 and band 72 represent the effect site concentration (EC) at which a particular drug will have its desired effect on range of percentages of a population (e.g., fifty percent (50%) to ninety-five percent (95%) of population normal), with the bottom of the shaded area representing the lowest portion (e.g., EC50) of the range and the top of the shaded area representing the high end (e.g., EC95) of the range.

When the drug is a sedative, a value such as EC50 may represent the concentration of the sedative at which there is a fifty percent (50%) probability that the population normal patient will be fully sedated, while EC95 may represent the concentration of the sedative at which there is a ninety-five percent (95%) probability that the population normal patient will be fully sedated. When full sedation is desired, the clinician may rely on the depicted model to determine the concentration at which there is something more than a ninety-five percent (95%) chance that the subject will be fully sedated. By providing a predictive graphic illustration of the sedative's current and future effect on a subject, the clinician may be able to better determine when to reduce the amount of sedative administered to the subject so that the subject may wake up (e.g., at some point below the EC50 portion of the band).

Wires 70 and 74 and, thus, band 72 may be moved by testing the subject to determine his, her, or its responsiveness to the sedative. A model according to the present invention may then be adjusted to assist the clinician in further administration of sedatives and other anesthesia.

In graphs that are configured to display effects of analgesics and neuromuscular blockers, similar reference points may be provided. For example, in graph 50', when intubation, or laryngoscopy, is necessary or desired, it is typically necessary to administer a relatively large quantity of one or more neuromuscular blockers to a subject. Thus, the effective site concentration (EC) wires 70a' and 74a' and band 72a' appear on graph 50' at much higher neuromuscular blocker concentrations than the corresponding (e.g., the same probabilities) reference points (i.e., wires 70b' and 74b' and band 72b' corresponding to the required effect site concentration of the same neuromuscular blocker to have the desired relaxant effect during a subject's post-operative recovery.

In the illustrated example, thick, vertically oriented bars, or indicators 60 and 60', respectively represent bolus administrations of 100 mg of propofol, a sedative, at a concentration of 2.63 .mu.g/kg/min. and 200 .mu.g of fentanyl, an analgesic, at a concentration of 2.29 ng/ml. Immediately after the initial bolus administrations, graph 50 shows, by way of indicators 62 and 62', that continuous intravenous administration of propofol was modeled at an administration rate of 100 .mu.g/kg/min. (i.e., 100 .mu.g per kg of body weight of the subject each minute). At a later point in time (e.g., about eight to ten minutes), continuous administration of another analgesic, remifentanil, was initiated. Modeling was based on administration of remifentanil having a concentration of 1.04 ng/ml at a rate of 0.20 .mu.g/kg/min.

As combined-drug effect lines 58 and 58' are located well above each wire 70, 70a', and 70b', graphs 50 and 50' clearly and intuitively indicate to a user of system 1 (FIG. 1) that the drug combination that has been modeled has an extremely high probability of providing all of the desired effects. In fact, graphs 50 and 50' indicate that it may be possible to reduce the amount of one or more of the administered drugs while still achieving the desired effects.

Example 2

Figure 7:
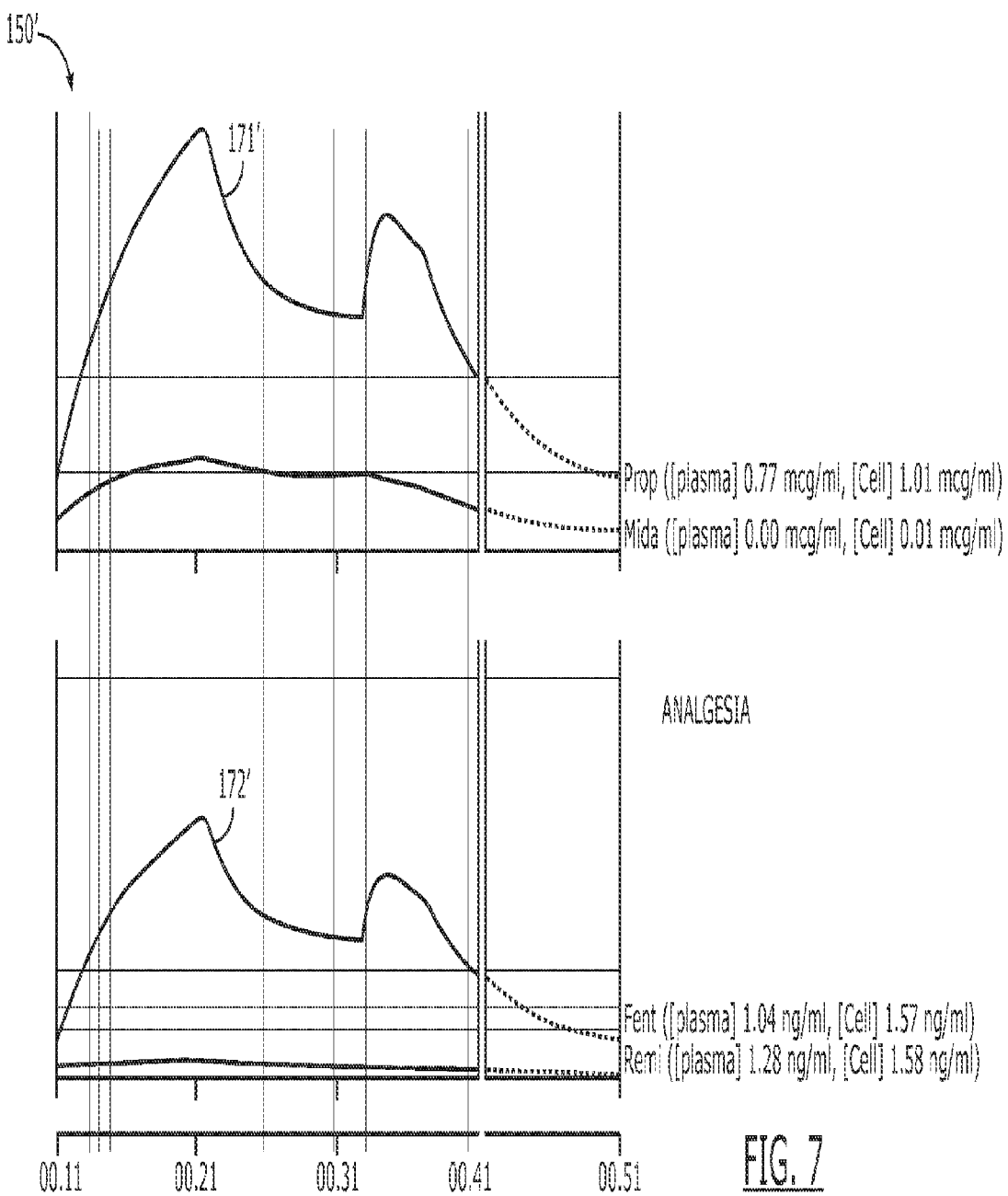
FIG. 7 is another embodiment of a two-dimensional display according to a specific embodiment of the present invention.

FIG. 7 shows a specific example of a three-dimensional graph 150 of synergistic interactions between two drugs, which model is characterized by response surface 155. Axes 152 and 154 represent the concentrations of the two drugs. Isoboles, or wires 170, 174, which extend horizontally across surface 155 and intersect axes 152 and 154, represent certain probabilities that combinations of the two drugs will achieve the same probability of response to a given stimulus. Each wire 170, 174 is made up of points (not depicted individually) representative of all of the different concentrations of each drug that will achieve the represented probability. Modeled information may be simulated over time, and presented as an intuitive visualization of concentrations and effects in the $P_k$-$P_d$ display (e.g., by points 156 (past), 157 (present), 158 (future)).

The data from FIG. 3 is shown in a two-dimensional format in the graph 150' of FIG. 7. Graph 150', in total, depicts a course of anesthesia that lasts for 40 minutes, including 30 minutes into the past (left) and 10 minutes into the future (right). Concentrations and effects are shown in categories of sedation and analgesia and in context of therapeutic windows (e.g., loss or return of consciousness (LOC/ROC), tracheal intubation, and post-operative analgesia). Line 171' represents the supra additive effect of propofol combined with remifentanil on sedation and line 172' represents the supra additive effect of propofol combined with remifentanil on analgesia. The vertical axes for lines 171' and 172' are in multiples of the EC50 for LOC and EC50 for laryngoscopy for lines 171' and 172', respectively. In FIG. 7, "Laryn" represents laryngoscopy, "SI" represents skin incision, "SM" represents surgical maintenance, "SC" represents skin closure, and "WC" represents wound closure.

Example 3

Time courses of different opioids may differ from one another, as may the pharmacokinetic profiles of different opioids. But the pharmacodynamic characteristics of different opioids are similar to one another. As a specific example, the fentanyl congener opioids (e.g., fentanyl, remifentanil, sufentanil, and alfentanil) have similar chemical formulas and act on the same receptors in the brain. Their differences in potency are thought to be linearly related and may differ depending on their pharmacodynamic.

Inhaled agents such as isoflurane, sevoflurane, and desflurane are potent anesthetics commonly used in the operating room. Using an anesthesia machine, these agents are vaporized and added to the patient's breathing circuit. As the patient breathes (or a ventilator breathes for the patient), the anesthetic vapor is transported into the bloodstream via the lungs and carried to the effect site in the brain. Inhaled agents primarily affect the patient's level of sedation, but they also have analgesic and neuromuscular effects.

Figure 8:
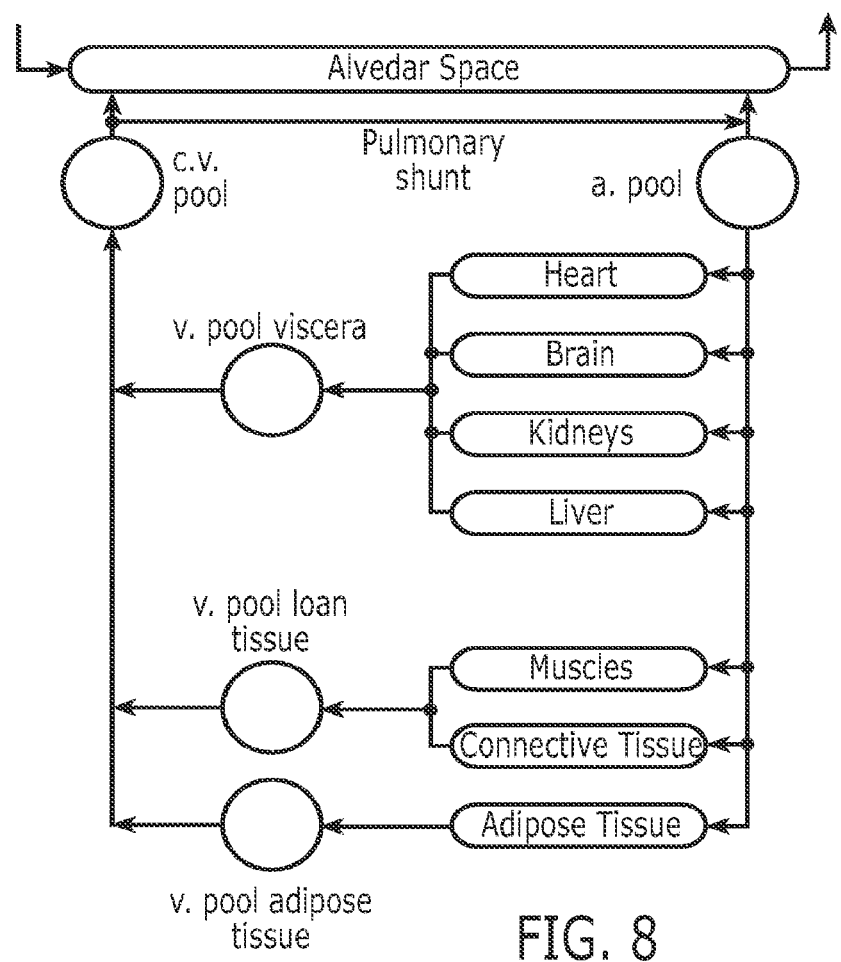
FIG. 8 is a multi-compartment $P_k$ model for inhaled agents.

A multiple compartment $P_k$ model for inhaled agents is shown in FIG. 8. Model compartments are divided into different tissues, including the brain. Partition, solubility coefficients and cardiac output determine the uptake and rate of change of agent for each compartment.

Thus, each of the inhaled agents has differing pharmacokinetics (different onset and time course of the drugs) but similar pharmacodynamic characteristics. Like opioids, the differences in potency are thought to be linearly related for sevoflurane, isoflurane, and desflurane. Potencies are often related in terms of the minimum alveolar concentration (MAC) to blunt response to skin incision in 50% of patients or the minimum alveolar concentration for 50% of patients to be asleep ($MAC_{awake}$).

Figure 9:
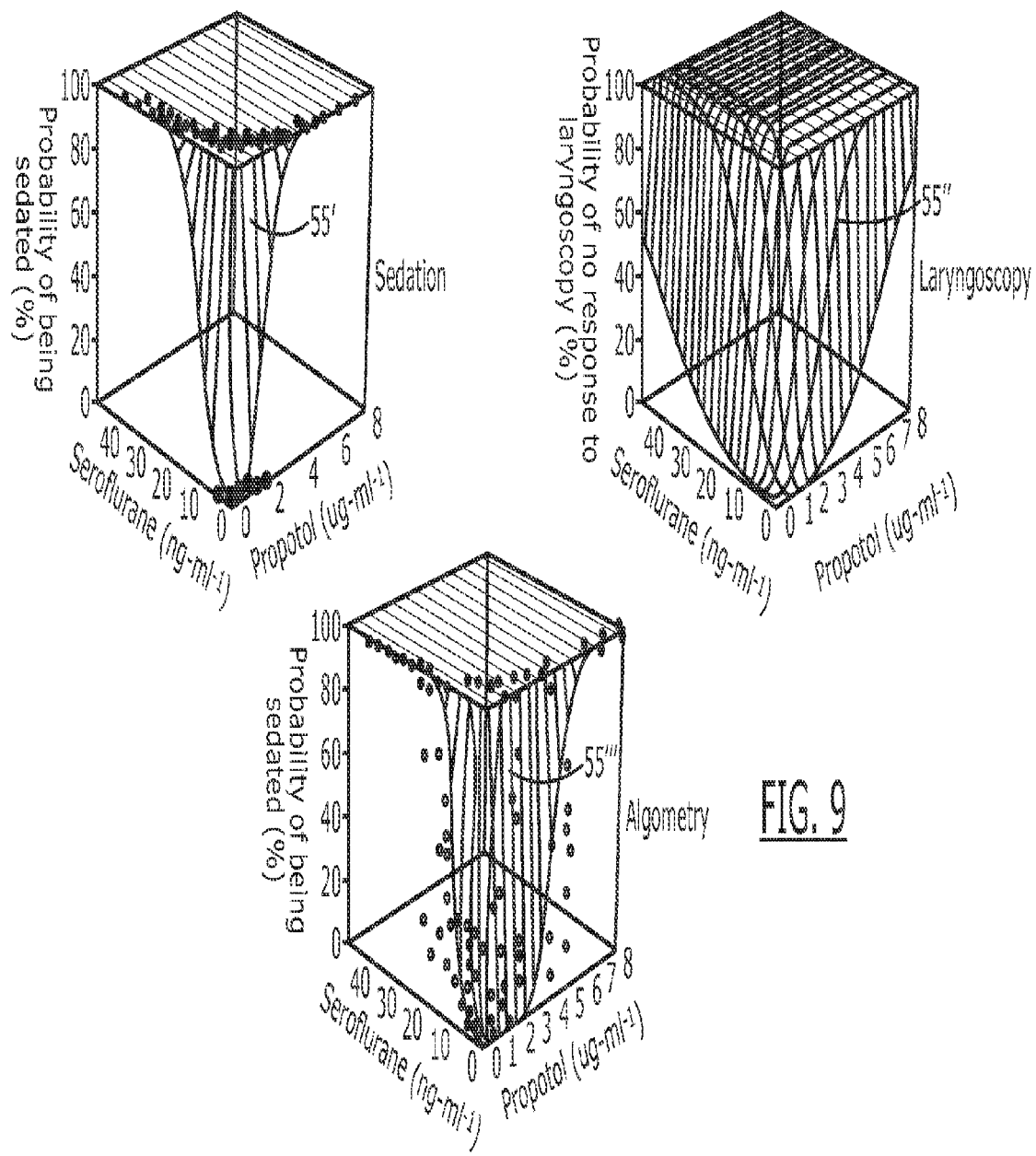
FIG. 9 shows three-dimensional displays of the combined sedative and analgesic effects of a specific example of a combination of drugs.

Inhaled agents interact synergistically with opioids as they produce both analgesic and hypnotic effects. The manner in which sedative-hypnotics and opioids interact over the complete range of clinical concentrations for sevoflurane and remifentanil have been assessed. The surrogate analgesic and hypnotic effect measures have been characterized in volunteers by using response surface analysis techniques. The response surfaces for sevoflurane and remifentanil are represented in FIG. 9 and include an OAA/S sedation scale surface 55', a laryngoscopy surface 55'', a tibial pressure algometry surface 55''', and, optionally, although not shown, an electrical (titanic) stimulus surface. The illustrated response surfaces 55', 55'', 55''' bow outward, indicating a synergistic interaction between sevoflurane and remifentanil.

Example 4

The sevoflurane-remifentanil $P_d$ response surface model will be generalized for multiple inhaled agents and multiple opioids using relative potency relationships. A $P_k$-$P_d$ display that incorporates teachings of the present invention will show model predictions for brain concentrations of each drug administered, as well as the probability of response of a subject to key clinical endpoints when certain inhaled agents are used in combination with specific opioids.

Example 4

Figure 10:
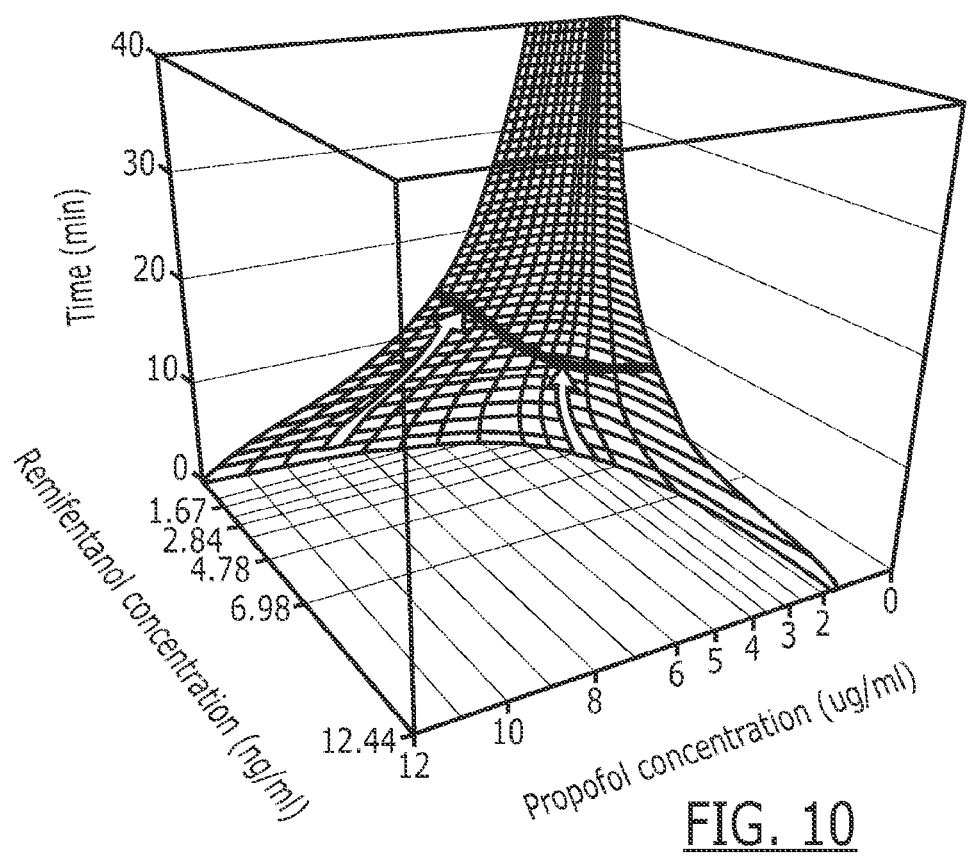
FIGS. 10 and 11 show use of a three-dimensional display to optimize a subject's wakeup time from anesthesia.

Response surface models, such as that depicted in FIG. 10, show that a number of combinations of the opioid and sedative produce the same level of anesthesia. Although the combinations produce the same level of anesthesia, their decrement times vary widely. For example, a combination that uses a high amount of propofol (sedative) and low amount of remifentanil (opioid) has a much slower decrement time than one that uses a lower amount of propofol (sedative) and higher remifentanil (opioid). The decrement or recovery time is dependent on a number of factors such as the kinetics of the drugs, relative potency and steepness of the concentration effect relationship and the nature of their interaction. It is possible to identify that one combination of a sedative-hypnotic and an opioid will have the fastest recovery from anesthesia. This ratio can be estimated by simulating anesthetic procedures using different combinations of opioid and sedative that produce the same level of anesthesia. The simulations are done by using $P_k$ models of the two drugs together with the response surface $P_d$ model. The time to recover from anesthesia estimated from simulation can be used to identify the optimal combination of opioid and sedative. These combinations meet the dual goal of providing an adequate level of anesthesia and fast emergence. By utilizing these combinations as a dosing guide, the clinician can provide a safe level of anesthesia while avoiding adverse effects associated with slow recovery. These optimization methods will be used as a template for real-time optimization of wakeup with adequate analgesia in the $P_k$-$P_d$ display.

This $P_k$-$P_d$ modeling information should form the scientific foundation of drug administration in anesthesiology and should be used to improve the quality and economy of anesthesia and reduce the risk of patient injury. For example, the $P_k$-$P_d$ modeling information could be incorporated into known target controlled infusion (TCI) devices, which are configured to intravenously deliver drugs.

Example 5

Figure 11:
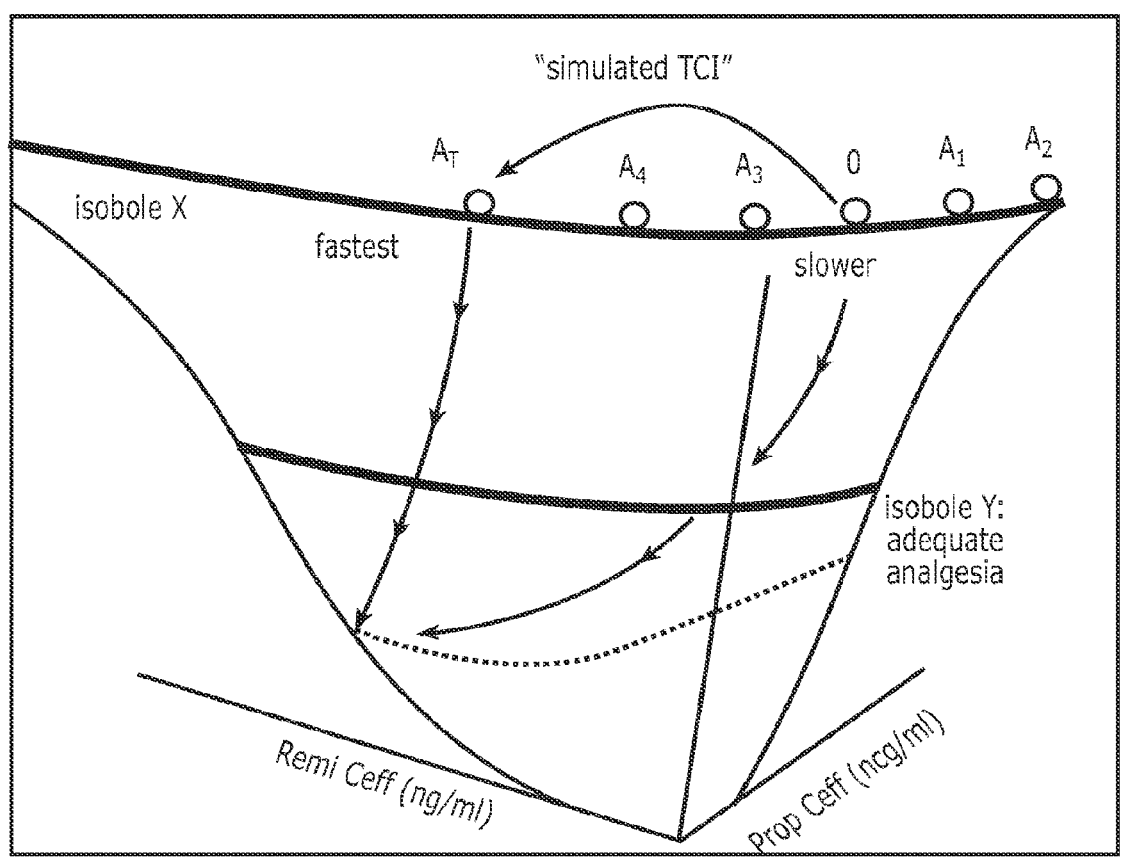

A real-time optimization algorithm may be used to identify the appropriate combination of drugs (e.g., remifentanil and propofol) and the manner of administration of the drugs to obtain or maintain a desired effect (e.g., providing adequate sedation and analgesia while minimizing patient wakeup time). For example, as shown in FIG. 11, during surgery a clinician might maintain the level of sedation at isobole X on the OAA/S<2 response surface, the display will identify the target propofol and remifentanil effect-site concentrations cp and cr, respectively, such that a present level of sedation remains unchanged (i.e., remains on isobole X), wakeup time is minimized when propofol administration is stopped, and levels of analgesia will be targeted for patient recovery with minimal postoperative pain without respiratory depression. This optimization is dependent on both drug kinetics and the synergistic interaction of one or more opioids and propofol. The propofol-remifentanil response surface models will be employed, with all opioid (e.g., fentanyl) effect-site concentrations being represented in "remifentanil equivalents" using known relative potency relationships.

FIG. 11 illustrates this example of an optimization method graphically. Point $A_0$ on isobole X represents the point where the clinician is presently maintaining anesthesia. Isobole Y represents the isobole of adequate analgesia, mapped on the OAA/S<2 response surface. For instance, Y might be chosen as the top threshold of the post-operative pain therapy window in the in the $P_k$-$P_d$ display of FIG. 11, which is defined as the 95% probability of non-response for the algometry. Point $A_T$ represents the optimal point to target when the clinician is ready to wake the patient, where propofol and remifentanil infusions will be stopped. Simulations of "wakeup" trajectories are performed to determine location $A_T$ on isobole X for reaching isobole Y the fastest. These simulations comprise theoretical $P_k$-$P_d$ simulations that are executed as a background process in the $P_k$-$P_d$ display. By way of example only, the simulations may be executed once in about every five seconds to once every 30 seconds. The optimal combination of drugs, their concentrations, and the manner and timing of their delivery will be shown on the $P_k$-$P_d$ display.

An optimization algorithm includes a calculation of the duration $T_0$ from present, at location $A_0$, until the subject is to wake up. Such a calculation includes setting an infusion rate for a first theoretical drug (e.g., propofol) to zero and targeting an effect-site concentration for a second theoretical drug (e.g., remifentanil) for adequate analgesia, which is the difference between the amount of the second theoretical drug (e.g., an opioid) needed to be at isobole Y at wakeup and amount of additional opioid (e.g., fentanyl or sufentanil) remaining on-board (i.e., in the subject's system) at the time of wakeup.

Additionally, the optimization algorithm includes calculating the durations $T_1, T_2, \ldots, T_N$ between the present time and a variety of targeted wakeup times is computed for each of the simulated end points $A_1$, $A_2, \ldots, A_N$. In calculating each of these durations, known target control infusion algorithms are used to traverse from $A_0$ to the point to be tested (e.g., $A_1$, $A_2, \ldots, A_N$). The wakeup time $T_1$, $T_2, \ldots, T_N$ is computed in a manner similar to that for calculating $T_0$.

The optimal point $A_T$ on isobole X is defined as the point $A_i$ with the lowest $T_i$, where $i=0, 1, \ldots, N$.

The optimization algorithm may be iterative, updating a new optimal target on a frequent basis (e.g., every minute). The recommendations provided by the optimization algorithm will be constrained to clinically relevant target pairs (e.g., $0.1=(cp/cr)=3$). The target range for cp and cr at $A_T$ will have tolerances defined as half the distance to the target's adjacent and less optimal drug pairs (e.g., if $A_3$ is the optimal point on the isobole, ranges will be defined for cp and cr such that they extend half the distance to A.sub.2 and half the distance to A.sub.4). Because the algorithm is iterative, the number of calculations per iteration may be minimized by constraining to search for drug pairs attainable within a specified time distance (e.g., three minutes) from the current location A.sub.0 on the surface.

Such an optimization algorithm may be used with a combination of propofol as sedative and remifentanil and/or fentanyl as analgesics, as well as for other combinations of drugs, including, but not limited to, anesthetic agents. For example, sevoflurane may be used in conjunction with opioids. Sevoflurane may be generalized to opioids by use of the relative potencies of opioid effect. In still another example, sevofluorane may be generalized to any of isoflurane, desflurane, and halothane using minimum-alveolar concentration equivalent potencies.

The target range for cp and cr at A.sub.T, as determined using an optimization algorithm, may be presented graphically in the P.sub.k-P.sub.d display, updated frequently (e.g., every minute).

Methods, models, and apparatus that incorporate teachings of the present invention are useful for a variety of purposes, including minimization of wakeup time following administration of anesthesia, avoidance of hypertensive and hypotensive episodes, fewer adjuvant drug interventions, a lower incidence of patient movement, and a lower incidence of the need for pharmacologic reversal of opioid effect to restore spontaneous ventilation. By generalizing P.sub.k-P.sub.d models for use with inhaled agents and opioids, the display will be useful in a significantly larger portion of administered anesthetics. By accounting for additional model covariates, such as opioid tolerant subjects, the display can provide accurate predictions for outliers beyond the normal population, possibly reducing risk of respiratory depression and inadequate analgesia. Optimizing the display will bring intelligence into the display, providing complex optimizations with a simple presentation to the user.

Although the examples provided herein primarily deal with modeling and administration of anesthetic drugs, methods, displays, and systems that incorporate teachings of the present invention may be used in conjunction with a variety of different types of drugs. Examples include, but are not limited to, cardiovascular drugs (e.g., epinephrine, dopamine, dobutamine, atropine, etc.), anti-arrhythmic drugs (lidocaine, etc.), diuretic drugs, and a variety of other types of drugs.

While the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. An apparatus for use in delivering anesthesia to a subject, comprising:
at least one input element configured to receive drug information regarding a plurality of anesthetic agents for administration to the subject from an anesthetist;
at least one input element configured to receive a target for sedative and analgesic effect from the anesthetist for maintenance of the anesthesia;
at least one input element configured to receive a target for analgesia versus wakeup time effect from the anesthetist;
a display; and
at least one processing element configured to receive the drug information and programmed to perform the method, the method comprising:
determining concentrations of the plurality of anesthetic agents, including interactions between anesthetic agents of the plurality, to achieve an optimal wakeup time for the subject based on a drug effect model accessed by the at least one processing element;
determining concentrations of the plurality of anesthetic agents based on the drug effect model accessed by the at least one processing element, including interactions between anesthetic agents, that will maintain or increase a current sedative and analgesic effect, and minimize the time it takes the subject to wake up after a surgical procedure is complete, and minimize pain awareness and risk of respiratory depression of the subject at and after the desired wakeup time; and
modeling at least present and future sedative and analgesic effects of determined concentrations of the plurality of anesthetic agents on the subject based on individual characteristics of the subject and the drug effect model; and
depicting on a display: the future sedative and analgesic effects of the determined concentrations; and synergies between the plurality of anesthetic agents; concentrations of the plurality of anesthetic agents for achieving the target sedative and analgesic effect and the target analgesia versus wakeup time effect; concentrations of the plurality of anesthetic agents that will maintain or increase a current sedative effect and lower a risk of respiratory depression of the subject for at least thirty minutes following wakeup; and indicators corresponding to a probability that the plurality of anesthetic agents will be within the desired range of effectiveness on the subject or on a specific part of the general population, the indicators being adjustable automatically or by user input when effectiveness of the plurality of anesthetic agents is different than anticipated or modeled, and the indicators including a lower range indicator below which the plurality of anesthetic agents are less likely to be within a desired range of effectiveness and an upper range indicator above which the plurality of anesthetic agents are more likely to be within the desired range of effectiveness.

2. The apparatus of claim 1, wherein the display depicts effects of at least one sedative, and at least one short-acting analgesic, and at least one long-acting analgesic.

3. The apparatus of claim 1, wherein the display depicts effects of a sedative comprising one or more of propofol, sevoflurane, desflurane, isoflurane, and halothane on the subject.

4. The apparatus of claim 1, wherein the display depicts effects of at least one analgesic comprising one or more of remifentanil, fentanyl, alfentanil, and sufentanil on the subject.

5. The apparatus of claim 1, wherein the at least one processing element is programmed to determine the concentrations of the plurality of anesthetic agents that will maintain a current sedative effect and minimize the time it takes the subject to wake up after a surgical procedure is complete.

6. The apparatus of claim 1, wherein the display is configured to depict the concentrations of the plurality of anesthetic agents that will minimize the time it takes the subject to wake up after a surgical procedure is complete.

7. The apparatus of claim 1, wherein the at least one processing element is programmed to determine concentrations of the plurality of anesthetic agents that will maintain a current analgesic effect and lower the pain awareness of the subject following wakeup.

8. The apparatus of claim 1, wherein the display is configured to depict the concentrations of the plurality of anesthetic agents that will lower a risk of the pain awareness of the subject.

9. The apparatus of claim 1, wherein the at least one input element is configured to receive data regarding at least one event that may provide an indication of an effect of the plurality of anesthetic agents on the subject and the at least one processing element is configured to cause the display to show the at least one event at a location that corresponds to a time of the at least one event and concentrations or effects of the plurality of anesthetic agents at that time.

10. The apparatus of claim 1, wherein the at least one processing element is further programmed to determine and cause to be displayed on the display a manner and timing for delivery of the plurality of anesthetic agents for achieving the target sedative and analgesic effect and the target analgesia versus wakeup time effect.

11. The apparatus of claim 1, wherein the at least one processing element is further programmed to determine the concentrations of the plurality of anesthetic agents for achieving the target sedative and analgesic effect based on physiological response parameters of the subject.

12. The apparatus of claim 1, wherein the at least one processing element is further programmed to determine the target sedative and analgesic effect based on the concentrations of the plurality of anesthetic agents.

13. The apparatus of claim 1, wherein the at least one processing element is programmed to determine the concentrations of the plurality of anesthetic agents that will maintain a current sedative and analgesic effect and lower a risk of respiratory depression of the subject for at least thirty minutes following wakeup.

14. The apparatus of claim 1, wherein the at least one processing element is programmed to determine the concentrations of the plurality of anesthetic agents that will maintain a current sedative and analgesic effect and lower pain awareness of the subject for at least thirty minutes following wakeup.

15. The apparatus of claim 1, wherein the display depicts concentrations of the plurality of anesthetic agents that will maintain or increase a current sedative effect and lower the time it takes the subject to wake up after a medical procedure is complete as determined by the at least one processing element.

16. The apparatus of claim 1, wherein the display depicts concentrations of the plurality of anesthetic agents that will lower pain awareness of the subject for at least thirty minutes following wakeup as determined by the at least one processing element.

17. The apparatus of claim 1, wherein the display includes a drug effect line and one or more of the indicators provide a user with an indication of modeled probability that a represented drug or drug combination will have a desired effect on the subject at a specific point in time as determined by the at least one processing element.

18. The apparatus of claim 1, wherein one or more of the indicators indicates whether a range of concentrations of the plurality of anesthetic agents is within a desired range of effectiveness as determined by the at least one processing element.

19. The apparatus of claim 1, wherein the lower range indicator corresponds to an approximately fifty percent (50%) probability that the plurality of anesthetic agents will be within the desired range of effectiveness on the subject or on a specific part of the general population.

20. The apparatus of claim 1, further comprising displaying physiological parameters of the subject over time with corresponding concentrations of the plurality of anesthetic agents and response parameters of the subject to the plurality of anesthetic agents.

* * * * *